(12) United States Patent
Williams et al.

(10) Patent No.: US 10,463,610 B2
(45) Date of Patent: Nov. 5, 2019

(54) COMPOSITION COMPRISING DIACID DERIVATIVES AND THEIR USE IN THE TREATMENT OF COLLAGENIC EYE DISORDERS

(71) Applicant: THE UNIVERSITY OF LIVERPOOL, Liverpool (GB)

(72) Inventors: Rachel L. Williams, Liverpool (GB); Colin E. Willoughby, Liverpool (GB)

(73) Assignee: The University of Liverpool, Liverpool (GB)

( * ) Notice: Subject to any disclaimer, the term of this patent is extended or adjusted under 35 U.S.C. 154(b) by 0 days.

(21) Appl. No.: 15/773,134

(22) PCT Filed: Nov. 3, 2016

(86) PCT No.: PCT/GB2016/053411
§ 371 (c)(1),
(2) Date: May 2, 2018

(87) PCT Pub. No.: WO2017/077300
PCT Pub. Date: May 11, 2017

(65) Prior Publication Data
US 2018/0318212 A1 Nov. 8, 2018

(30) Foreign Application Priority Data

Nov. 3, 2015 (GB) .................................. 1519450.9

(51) Int. Cl.
| | | |
|---|---|---|
| *A61K 31/19* | (2006.01) | |
| *A61K 9/00* | (2006.01) | |
| *A61K 31/191* | (2006.01) | |
| *A61K 31/335* | (2006.01) | |
| *A61P 27/02* | (2006.01) | |
| *A61K 31/194* | (2006.01) | |
| *A61K 31/4025* | (2006.01) | |
| *A61K 47/18* | (2017.01) | |
| *A61K 47/12* | (2006.01) | |
| *A61K 9/08* | (2006.01) | |

(52) U.S. Cl.
CPC .............. *A61K 9/0048* (2013.01); *A61K 9/08* (2013.01); *A61K 31/191* (2013.01); *A61K 31/194* (2013.01); *A61K 31/335* (2013.01); *A61K 31/4025* (2013.01); *A61K 47/12* (2013.01); *A61K 47/18* (2013.01); *A61P 27/02* (2018.01)

(58) Field of Classification Search
CPC ...................................................... A61K 31/19
See application file for complete search history.

(56) References Cited

U.S. PATENT DOCUMENTS

| | | | | |
|---|---|---|---|---|
| 7,799,782 B2 * | 9/2010 | Munson | ............... | C07D 231/56 514/234.5 |
| 2008/0275000 A1 * | 11/2008 | Xia | ...................... | A61K 9/0048 514/54 |
| 2011/0086802 A1 * | 4/2011 | Dewoolfson | ........ | A61K 31/185 514/17.2 |
| 2014/0271897 A1 | 9/2014 | Pathak | | |

FOREIGN PATENT DOCUMENTS

| | | |
|---|---|---|
| EP | 0443094 A2 | 8/1991 |
| WO | WO-99/39238 A1 | 8/1999 |
| WO | WO-2009/120549 A2 | 10/2009 |

OTHER PUBLICATIONS

Chen et al.,Journal of Mass Spectrometry, 2013, 48(7):807-812.*
Chen et al., "Understanding Chemical Reactivity for Homo- and Heterobifunctional Protein Cross-Linking Agents," Journal of Mass Spectrometry, 48(7):807-812 (2013).
International Search Report and Written Opinion for International Application No. PCT/GB/2016/053411 dated Jan. 20, 2017.
Bax et al., "Fundamental insight into the effect of carbodiimide crosslinking on cellular recognition of collagen-based scaffolds," Acta biomaterialia, 49:218-234 (2017).
Khutoryanskaya et al., "Hydrogen-Bonded Complexes and Blends of Poly (acrylic acid) and Methylcellulose: Nanoparticles and Mucoadhesive Films for Ocular Delivery of Riboflavin," Macromolecular bioscience,14(2):225-234 (2014).
Lai et al., "Synthesis, characterization and ocular biocompatibility of potential keratoprosthetic hydrogels based on photopolymerized poly (2-hydroxyethyl methacrylate)-co-poly (acrylic acid)," Journal of Materials Chemistry, 22(5):1812-1823 (2012).
Luman et al., "Dendritic polymers composed of glycerol and succinic acid: Synthetic methodologies and medical applications," Pure and applied chemistry, 76(7-8):1375-1385 (2004).
Mitra et al., "Di-carboxylic acid cross-linking interactions improves thermal stability and mechanical strength of reconstituted type I collagen: Part I. Oxalic acid," Journal of thermal analysis and calorimetry, 105:325-330 (2011).
Mitra et al., "Preparation and characterization of malonic acid cross-linked chitosan and collagen 3D scaffolds: an approach on non-covalent interactions," Journal of Materials Science: Materials in Medicine, 23(5):1309-1321 (2012).
Mitra et al., "Studies on cross-linking of succinic acid with chitosan/collagen." Materials Research, 16(4):755-765 (2013).
Oelker et al., "Synthesis and characterization of dendron cross-linked PEG hydrogels as corneal adhesives," Biomacromolecules, 12(5):1658-1665 (2011).
Rhee et al., "In vivo stability of poly (ethylene glycol) collagen composites," Poly (Ethylene Glycol), 680:420-440 (1997).

(Continued)

*Primary Examiner* — Rei Tsang Shiao
(74) *Attorney, Agent, or Firm* — Foley Hoag LLP; David P. Halstead; Lucas P. Watkins

(57) ABSTRACT

The present invention relates to novel pharmaceutical formulations. More specifically, the present invention relates to novel pharmaceutical formulations that are suitable for intraocular administration. The present invention also relates to the use of these formulations for the treatment of collagenic eye disorder such as, for example, the treatment of keratoconus.

20 Claims, 27 Drawing Sheets

(56) References Cited

OTHER PUBLICATIONS

Sailakshmi et al., "Suberic acid acts as a dissolving agent as well as a crosslinker for natural polymers (carbohydrate and protein): a detailed discussion on the chemistry behind the interaction," Journal of Macromolecular Science, 49:619-629 (2012).
Saito et al., "pH-responsive swelling behavior of collagen gels prepared by novel crosslinkers based on naturally derived di-or tricarboxylic acids," Acta biomaterialia, 3:89-94 (2007).
Shen et al., "Influence on the physicochemical properties of fish collagen gels using self-assembly and simultaneous cross-linking with the N-hydroxysuccinimide adipic acid derivative," Connective tissue research, 56(3):244-252 (2015).
Sripriya et al.,"Characterizations of polyanionic collagen prepared by linking additional carboxylic groups," Reactive and Functional Polymers, 71(1):62-69 (2011).
Zhang et al., "The rheological and structural properties of fish collagen cross-linked by N-hydroxysuccinimide activated adipic acid," Food hydrocolloids, 30(2):504-511 (2013).

\* cited by examiner a)

b)

COMPOSITION COMPRISING DIACID DERIVATIVES AND THEIR USE IN THE TREATMENT OF COLLAGENIC EYE DISORDERS

REFERENCE TO RELATED APPLICATIONS

This application is the U.S. National Stage of International Patent Application No. PCT/GB2016/053411, filed Nov. 3, 2016, which claims the benefit of and priority to Great Britain Patent Application No. 1519450.9, filed Nov. 3, 2015. The International Patent Application is hereby fully incorporated by reference herein.

FIELD OF THE INVENTION

The present invention relates to a novel treatment for collagenic eye disorders, especially disorders associated with collagen in the cornea and sclera, such as, for example, keratoconus. The present invention also relates to a pharmaceutical formulation that is suitable for administration to the eye for the treatment of collagenic eye disorders.

BACKGROUND OF THE INVENTION

Collagen-containing connective tissues play a fundamental role in maintaining the correct structure and function of the eye. The importance of collagen in the eye is demonstrated by its natural abundance, with approximately 80% of the eye comprising collagen. The properties of collagen, namely its strength and elasticity, help maintain the curved geometry of the eye ball, which is necessary for the eye to function properly.

In addition, collagen also helps the eye ball cope with changes in internal pressure by maintaining the necessary rigidity and elasticity that prevent the eye from bursting/rupturing and/or collapsing.

The weakening and/or degradation of structural proteins (such as collagen) in the eye is symptomatic of a number of eye disorders (referred to herein as collagenic eye disorders). Illustrative examples of collagenic eye disorders include various forms of corneal ectasia (non-inflammatory corneal ectasia, e.g. keratoconus, keratoglobus, pellucid marginal degeneration; inflammatory corneal ectasia; iatrogenic corneal ectasia (keratectasia), e.g. following laser refractive procedures/refractive surgery (LASIK, LASEK, PRK); or myopia). In addition, collagenic eye disorders include disorders in which the collagen in the eye, particularly the cornea or sclera, is weakened and/or degraded as a consequence of inflammation, infection, injury or corneal oedema.

By way of example, keratoconus is a degenerative disorder that results in a weakening of the collagen in the eye, which ultimately leads to progressive distortions in the shape of the eye ball. This progressive change in the eye's shape causes the eye to adopt a more conical shape over time which, in severe cases, can result in visual deterioration and eventual blindness.

Current methodologies for the treatment of keratoconus, and other related disorders, seek to strengthen the weakened collagen by photochemically cross-linking the collagen with riboflavin (vitamin B2). This technique, commonly known as corneal cross-linking or CXL. The procedure involves the application of riboflavin to the eye followed by exposure to UV radiation to initiate the photochemical cross-linking of the collagen with the riboflavin. However, the exposure of the eye to UV radiation can result in damage to the corneal endothelium and/or epithelium. In the most severe cases, retinal degeneration can occur. The CXL procedure also requires the top layer of the epithelium of the eye to be removed in order to enhance riboflavin penetration into the corneal stroma. The removal of the top layer of the epithelium from the eye requires delicate surgical techniques and also carries a risk of infection. As a consequence, specially trained medical practitioners and equipment are required in order to treat keratoconus and related disorders.

There is, therefore, a need for improved approaches for treating collagenic eye disorders in which cross-linking of collagen in the cornea and/or the sclera of the eye is beneficial.

The present invention was devised with the foregoing in mind.

SUMMARY OF THE INVENTION

The present invention provides a novel treatment for collagenic eye disorders such as, for example, keratoconus.

Thus, according to a first aspect of the invention, there is provided a pharmaceutical composition suitable for administration to the eye, comprising:
  (i) an aqueous vehicle;
  (ii) a non-toxic, water soluble cross-linker comprising two or more carboxyl groups and/or one or more anhydride groups and/or one or more ester groups, or a pharmaceutically acceptable salt thereof, dissolved in the aqueous vehicle;
and wherein the composition has a pH within the range of 6 to 9.

In another aspect, the present invention provides a pharmaceutical composition as defined herein for use in the treatment of a collagenic eye disorder.

In another aspect, the present invention provides a method of treating a collagenic eye disorder, said method comprising administering to a human or animal subject in need of such treatment a therapeutically effective amount of a pharmaceutical composition as defined herein.

In another aspect, the present invention provides a non-toxic, water soluble cross-linker comprising two or more carboxyl groups and/or one or more anhydride groups and/or one or more ester groups, or a pharmaceutically acceptable salt thereof, for use in the treatment of a collagenic eye disorder. Suitably, the cross-linker is administered in combination with one or more peptide coupling reagents.

In another aspect, the present invention provides a method of treating a collegenic eye disorder, said method comprising administering to a human or animal subject in need of such treatment a therapeutically effective amount of a non-toxic, water soluble cross-linker comprising two or more carboxyl groups and/or one or more anhydride groups and/or one or more ester groups, or a pharmaceutically acceptable salt thereof. Suitably, the cross-linker is administered in combination with one or more peptide coupling reagents.

In yet another aspect, the present invention provides a device for administering a pharmaceutical composition as defined herein to the eye, the device comprising:
  (i) a first compartment comprising a pharmaceutical composition as defined herein;
  (ii) a second compartment comprising one or more peptide coupling agents dissolved in a suitable pharmaceutically acceptable vehicle;
  wherein the device is configured to mix at least a proportion of the contents of the first and second compartments either prior to or during dispensing to the eye.

DETAILED DESCRIPTION OF THE INVENTION

Definitions

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Unless otherwise stated, the following terms used in the specification and claims have the following meanings set out below.

The terms "treating" or "treatment" include prophylaxis as well as the alleviation of established symptoms of a disease or condition. "Treating" or "treatment" therefore includes: (1) preventing or delaying the appearance of clinical symptoms of the disease or condition developing in a subject that may be afflicted with or predisposed to the disease or condition, but does not yet experience or display clinical or subclinical symptoms of the disease or condition, (2) inhibiting the disease or condition, i.e., arresting, reducing or delaying the development of the disease or condition or a relapse thereof (in case of maintenance treatment) or at least one clinical or subclinical symptom thereof, or (3) relieving or attenuating the disease or condition, i.e., causing regression of the disease or condition or at least one of its clinical or subclinical symptoms.

Unless otherwise specified, where the quantity or concentration of a particular component of a given formulation is specified as a weight percentage (wt. % or % w/w), said weight percentage refers to the percentage of said component by weight relative to the total weight of the formulation as a whole. It will be understood by those skilled in the art that the sum of weight percentages of all components of a formulation will total 100 wt. %. However, where not all components are listed (e.g. where formulations are said to "comprise" one or more particular components), the weight percentage balance may optionally be made up to 100 wt % by unspecified ingredients (e.g. a diluent, such as water, or other non-essential but suitable additives).

In this specification the term "alkyl" includes both straight and branched chain alkyl groups. References to individual alkyl groups such as "propyl" are specific for the straight chain version only and references to individual branched chain alkyl groups such as "isopropyl" are specific for the branched chain version only. For example, "(1-6C)alkyl" includes (1-4C)alkyl, (1-3C)alkyl, propyl, isopropyl and t-butyl.

The term "(m-nC)" or "(m-nC) group" used alone or as a prefix, refers to any group having m to n carbon atoms.

The term "carboxyl group" refers to an organic functional group consisting of a carbon atom double bonded to an oxygen atom and single bonded to a hydroxyl group. Thus the "carboxyl group" refers to an organic functional group of the formula $CO_2H$. For the avoidance of doubt, the term "carboxyl group" does not include any other organic functional groups comprising a carbonyl (C=O), such as, for example, aldehydes or ketones.

Throughout the specification, the term "ester" refers to an organic functional group of the formula C(O)OR, where R is a group other than hydrogen. Suitably, the ester is a hydrolysable ester, i.e. an ester that is capable of undergoing hydrolysis to form a carboxylic acid. Thus, the OR functional group of the ester is suitably a leaving group. Examples of R include, for example, (1-6C)alkyl, succinimide, 3-sulfo-succinimide or pentafluorophenyl, in particular, succinimide and 3-sulfo-succinimide.

Unless otherwise stated, the term "collagenic eye disorder" refers to eye disorders that are associated with the weakening, degradation and/or damage to structural proteins, such as collagen, in the eye. Although it will be appreciated by a person skilled in the art that collagen is the main structural protein referred to herein, it will be understood that the term "collagenic eye disorder" also encompasses eye disorders associated with the weakening, degradation and/or damage of collagen in combination with other structural proteins in the eye. Furthermore, the term encompasses the weakening, degradation and/or damage to all parts of the eye, such as, for example, the cornea and the sclera.

Compositions of the Present Invention

As previously stated, the present invention provides a pharmaceutical composition that is suitable for administration to the eye for the treatment of collagenic eye disorders, such as, for example, keratoconus.

In a first aspect, the invention provides a pharmaceutical composition suitable for administration to the eye (ocular administration) comprising:
  (i) an aqueous vehicle; and
  (ii) a non-toxic, water soluble cross-linker comprising two or more carboxyl groups and/or one or more anhydride groups and/or one or more ester groups, or a pharmaceutically acceptable salt thereof, dissolved in the aqueous vehicle;
wherein the composition has a pH within the range of 6 to 9.

In an embodiment, the pH of the composition is within the range 6 to 8. In a further embodiment, the pH of the composition is within the range 6 to 7.5. In a further embodiment, the pH of the composition is within the range 6.5 to 7.5. In a preferred embodiment, the pH of the composition is within the range 7.0 to 7.5 (e.g. pH 7.4).

Cross-linker

The cross-linkers of the present invention are stable in the pharmaceutical compositions defined herein and display excellent levels of collagen cross-linking, especially when they are administered in combination with one or more peptide coupling agents. The cross-linkers of the present invention are also water soluble and non-toxic, making them particularly well suited for use in the treatment of collagenic eye disorders. Furthermore, when compared to the established corneal crosslinking (CXL) procedures, the crosslinkers of the present invention do not require any UV radiation in order to initiate the cross-linking and they can be administered to the eye without the need to remove the top layer of the epithelium. The cross-linkers of the present invention are therefore viable alternative agents for the treatment of collagenic eye disorders, such as, for example, keratoconus.

The cross-linkers of the present invention are non-toxic and water soluble. It will be understood by a person skilled in the art that water solubility is fundamental in allowing the cross-linker to effectively penetrate/permeate into the collagen tissue of the eye. Suitably, the cross-linkers of the present invention are also biocompatible.

In an embodiment, the non-toxic, water soluble cross-linker comprises two or more carboxyl groups and/or one or more anhydride groups, or a pharmaceutically acceptable salt thereof.

In an embodiment of the present invention, the non-toxic, water soluble cross-linker comprises two or more carboxyl groups. It will be understood that any two adjacent carboxyl groups in the cross-linker of the present invention may be linked to form an anhydride, as represented in Formula (II) below.

In another embodiment the non-toxic, water soluble cross-linker comprises 2 to 4 carboxyl groups. Suitably, the non-toxic, water soluble cross-linker is a di- or tri-carboxylic acid. Most suitably, the non-toxic, water soluble cross-linker is a dicarboxylic acid.

In another embodiment the non-toxic, water soluble cross-linker comprises 2 to 4 ester groups. Suitably, the non-toxic, water soluble cross-linker comprises 2 ester groups.

In another embodiment of the present invention, the non-toxic, water soluble cross-linker is a compound of Formula (I) or Formula (II) shown below, or a pharmaceutically acceptable salt and/or solvate thereof:

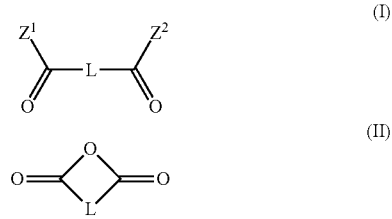

wherein L is a suitable linking group; and
$Z^1$ and $Z^2$ are independently selected from OH or OR, wherein R is selected from (1-6C)alkyl, succinimide, 3-sulfo-succinimide or pentafluorophenyl.

In another embodiment, $Z^1$ and $Z^2$ are independently selected from OH or OR, wherein R is selected from succinimide or 3-sulfo-succinimide.

In yet another embodiment, $Z^1$ and $Z^2$ are the same and are selected from OH or OR, wherein R is selected from succinimide or 3-sulfo-succinimide.

In yet another embodiment, $Z^1$ and $Z^2$ are OR, wherein R is selected from succinimide or 3-sulfo-succinimide.

In still another embodiment, $Z^1$ and $Z^2$ are OH.

In a particular embodiment of the present invention, the non-toxic, water soluble cross-linker is a compound of Formula (I) or Formula (II) shown below, or a pharmaceutically acceptable salt and/or solvate thereof:

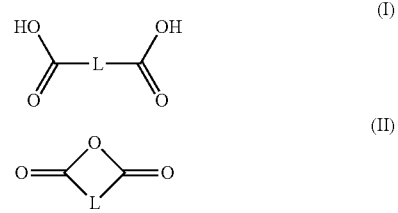

wherein L is a suitable linking group.

In an embodiment, the non-toxic, water soluble cross-linker is a compound of Formula (I).

In an embodiment, the non-toxic, water soluble cross-linker is a compound is not glutaric anhydride.

L may be any suitable linking group that connects the two carboxyl groups shown in Formula I or the two carbon atoms of the anhydride shown in Formula II.

The linking group L may be linear or branched. L may also be further substituted with one or more substituent groups. For example, L may be substituted with one or more substituent groups selected from carboxy, anhydride, oxo, halo, trifluoromethyl, cyano, nitro, hydroxy, mercapto, amino, (1-6C)alkyl, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, (2-6C)alkanoyl, or (2-6C)alkanoyloxy.

In an embodiment, L is unsubstituted or comprises one or more carboxyl or anhydride substituents.

In an embodiment, L is selected from:
(i) a linear or branched (1-12C)alkylene linker that optionally comprises one or more heteroatoms selected from N, O or S, and is optionally substituted with one or more groups selected from carboxy, anhydride, oxo, halo, trifluoromethyl, cyano, nitro, hydroxy, mercapto, amino, (1-6C)alkyl, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, (2-6C)alkanoyl, or (2-6C)alkanoyloxy, or
(ii) a water soluble polymeric chain (e.g. polyethylene glycol).

Particular cross-linkers of the invention include, for example, cross-linkers of the formula (I) or (II), or pharmaceutically acceptable salts and/or solvates thereof, wherein, unless otherwise stated, L, and any associated substituent group has any of the meanings defined hereinbefore or in any of paragraphs (1) to (11) hereinafter:—

(1) L is selected from:
(i) a linear or branched (1-12C)alkylene linker that optionally comprises one or more heteroatoms selected from N, O or S, and is optionally substituted with one or more groups selected from oxo, carboxy or anhydride;
(ii) a water soluble polymeric chain (e.g. polyethylene glycol).

(2) L is selected from:
(i) a linear (1-12C)alkylene linker that optionally comprises one or more 0 atoms, and is optionally substituted with one or more oxo or —$(CH)_n$—$CO_2H$ groups, wherein n is 0-10; or
(ii) a water soluble polymeric chain (e.g. polyethylene glycol).

(3) L is selected from:
(i) a linear (1-12C)alkylene linker that is optionally substituted with one or more —$(CH)_n$—$CO_2H$ groups, wherein n is 0-10; or
(ii) a polyethylene glycol chain.

(4) L is selected from:
   (i) a linear (1-12C)alkylene linker that is optionally substituted with one or more $-(CH)_n-CO_2H$ groups, wherein n is 0-10; or
   (ii) a polyethylene glycol chain comprising between 2 and 20 repeat units.
(5) L is selected from:
   (i) a linear (1-12C)alkylene linker that is optionally substituted with one or more $-(CH)_n-CO_2H$ groups, wherein n is 0-10; or
   (ii) a polyethylene glycol chain comprising between 2 and 10 repeat units.
(6) L is a (1-10C)alkylene optionally substituted with one or more $-(CH_2)_nCO_2H$ groups, wherein n is 0-10;
(7) L is a (2-8C)alkylene optionally substituted with one or more $-(CH_2)_nCO_2H$ groups, wherein n is 0-10;
(8) L is a (2-8C)alkylene optionally substituted with one or more groups of the formula $-(CH_2)_nCO_2H$, and wherein n is an integer of between 0 and 8;
(9) L is a (2-8C)alkylene optionally substituted with one or more oxo groups;
(10) L is selected from a (1-12C)alkylene or a polyethylene glycol chain comprising between 2 and 10 repeat units;
(11) L is a (1-12C)alkylene;
(12) L is selected from a (1-10C)alkylene or a polyethylene glycol chain comprising between 2 and 10 repeat units;
(13) L is a (1-10C)alkylene;
(14) L is selected from a (2-8C)alkylene or a polyethylene glycol chain comprising between 3 and 6 repeat units;
(15) L is a (2-8C)alkylene;
(16) L is selected from a (6-8C)alkylene or a polyethylene glycol chain comprising 5 repeat units; or
(17) L is a (6-8C)alkylene.

In another embodiment of the present invention, the non-toxic, water soluble cross-linker is a compound of formula (I) shown above, or a pharmaceutically acceptable salt and/or solvate thereof, wherein L is a (1-12C)alkyl optionally substituted with one or more groups of the formula $-(CH_2)_nCO_2H$, wherein n is an integer of between 0 and 10.

In an embodiment of the compounds of formula (I), L is as defined in any one of paragraphs (1) to (11) above. In a further embodiment, L is defined as in any one of paragraphs (4) to (11) above. In yet another embodiment, L is as defined in any one of paragraphs (7) to (11) above.

To further enhance the solubility of the cross-linkers of the present invention in water, L in the formulae (I) and (II) shown above may be replaced by a water soluble polymer (e.g. a polyethylene glycol (PEG) chain). It will be understood that any size of water soluble polymer (e.g. a polyethylene glycol (PEG)) may be used. In an embodiment, the water soluble polymer (e.g. a polyethylene glycol (PEG) chain) is less than 100 repeat (monomeric) units long. In another embodiment, the water soluble polymer (e.g. a polyethylene glycol (PEG) chain) is less than 50 repeat units long. In yet another embodiment, the water soluble polymer (e.g. a polyethylene glycol (PEG) chain) is less than 25 repeat units long. In still another embodiment, the water soluble polymer (e.g. a polyethylene glycol (PEG) chain) is less than 15 repeat units long. In a further embodiment, the water soluble polymer (e.g. a polyethylene glycol (PEG) chain) is less than 10 repeat units long.

In an embodiment, L is a polyethylene glycol chain with between 2 and 20 repeat units. Suitably, L is a polyethylene glycol chain with between 2 and 10 repeat units. More suitably, L is a polyethylene glycol chain with between 3 and 6 repeat units. Most suitably, L is a polyethylene glycol chain with 5 repeat units.

In an embodiment, the non-toxic, water soluble cross-linker has a molecular weight of less than 500. In a further embodiment, the cross-linker has a molecular weight of less than 400. In a further embodiment, the cross-linker has a molecular weight of less than 300. In a further embodiment, the cross-linker has a molecular weight of less than 250.

It will, however, be understood that in embodiments where L is a water soluble polymer (e.g. a polyethylene glycol (PEG)) chain, the molecular weight of the cross-linker may be increased beyond 500, since the increase in chain length is unlikely to adversely affect the water solubility of the cross-linker.

In a particular embodiment, the non-toxic, water soluble cross-linkers of the present invention are selected from bis(succinimidyl)penta(ethylene glycol), sebacic, azelaic, suberic, pimelic, adipic, glutaric, succinic acid, malonic or oxalic acid. Suitably, the non-toxic, water soluble cross-linkers of the present invention are selected from sebacic, azelaic, suberic, pimelic, adipic, glutaric, succinic acid, malonic or oxalic acid. More suitably, the non-toxic, water soluble cross-linkers of the present invention are selected from bis(succinimidyl)penta(ethylene glycol), sebacic, azelaic, suberic, pimelic or adipic acid. Yet more suitably, the non-toxic, water soluble cross-linkers of the present invention are selected from sebacic, azelaic, suberic, pimelic or adipic acid. Even more suitably, the non-toxic, water soluble cross-linkers of the present invention are selected from bis(succinimidyl)penta(ethylene glycol), adipic, sebacic or suberic acid. Most suitably, the non-toxic, water soluble cross-linkers of the present invention are selected from adipic, sebacic or suberic acid.

The cross-linker of the present invention may be present at any suitable concentration. In an embodiment, the concentration of the cross-linker in the pharmaceutical composition of the present invention is between 0.1 and 100 mM. Suitably, the concentration of the cross-linker in the pharmaceutical composition of the present invention is between 0.1 and 50 mM. More suitably, the concentration of the cross-linker in the pharmaceutical composition of the present invention is between 0.1 and 25 mM. Yet more suitably, the concentration of the cross-linker in the pharmaceutical composition of the present invention is between 0.5 and 20 mM. Most suitably, the concentration of the cross-linker in the pharmaceutical composition of the present invention is between 1 and 15 mM.

A suitable pharmaceutically-acceptable salt of a cross-linker of the invention is, for example, an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine. A further suitable pharmaceutically-acceptable salt of a cross-linker of the invention is, for example, a salt formed within the human or animal body after administration of a cross-linker of the invention.

A suitable pharmaceutically-acceptable solvate of a cross-linker of the invention is, for example, a hydrate such as a hemi-hydrate, a mono-hydrate, a di-hydrate or a tri-hydrate or an alternative quantity thereof.

The cross-linker of the invention may be administered in the form of a pro-drug, which is a compound that is broken down in the human or animal body to release a compound of the invention. A pro-drug may be used to alter the physical properties and/or the pharmacokinetic properties of a cross-linker of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a cross-linker of the invention and in vivo cleavable amide derivatives that may be formed at a carboxy group or an amino group in a cross-linker of the invention.

Accordingly, the present invention includes those cross-linker of the invention as defined hereinbefore when made available by organic synthesis and when made available within the human or animal body by way of cleavage of a pro-drug thereof. Accordingly, the present invention includes those cross-linker of the invention that are produced by organic synthetic means and also such compounds that are produced in the human or animal body by way of metabolism of a precursor compound, that is a cross-linker of the invention may be a synthetically-produced compound or a metabolically-produced compound.

Aqueous Vehicle

The non-toxic, water soluble cross-linkers of the present invention are dissolved, either fully or partially, in an aqueous vehicle. The term 'aqueous vehicle' can be understood to mean a liquid vehicle which predominately contains water.

The aqueous vehicle may therefore comprise greater than about 50% by volume of water. For example, the aqueous medium may contain more than 60% by volume water, e.g. more than 75% by volume water or more than 95% by volume water. Typically, the aqueous vehicle will comprise between 75 to 100% by volume of water.

The 'aqueous vehicle' may also comprise other solvents. It may therefore comprise organic solvents which may be fully or partially miscible with water. The aqueous medium may comprise solvents which are miscible with water, for example alcohols (e.g. methanol and ethanol). The aqueous medium may also comprise additives which may be ionic, organic or amphiphillic. Examples of such additives include surfactants, viscosity modifiers, tonicity agents, sterilising agents and a solubility enhancers.

Non-limiting examples of suitable surfactants include stearates, glycerides and cyclodextrins.

In an embodiment, the aqueous vehicle comprises a solubility enhancer, such as, for example, dimethylethanolamine (DMEA), N-methylmorpholine (NMM) or N-ethylmorpholine (NEM). Suitably, the solubility enhancer is dimethylethanolamine (DMEA).

Buffer

The pharmaceutical composition of the present invention suitably comprises a buffer in order to maintain the composition at a pH compatible for use in the eye.

In an embodiment, a suitable buffer is present to maintain the composition in the pH range 6 to 9. In a further embodiment, the buffer maintains the composition in the pH range 6 to 8. In another embodiment, the buffer maintains the composition in the pH range 6 to 7.5. In another embodiment, the buffer maintains the composition in the pH range 6.5 to 7.5. In another embodiment, the buffer maintains the composition in the pH range 7.0 to 7.5 (e.g. pH 7.4).

It will be understood that any suitable buffer may be used. In an embodiment, the buffer is selected from the group comprising: phosphate, acetate, citrate, sulfonic acid, ascorbate, linolenate, carbonate and bicarbonate based buffers. In a further embodiment, the buffer is selected from the group comprising: phosphate, acetate, citrate, sulfonic acid, carbonate and bicarbonate based buffers. In a particular embodiment, the buffer is phosphate buffered saline (PBS).

Peptide Coupling Reagent

It will be understood by a person skilled in the art that the crosslinking of biological material (e.g. collagen) by the compositions of the present invention is mediated through the reaction of carboxyl (or anhydride) groups on the cross-linkers with amino functionalities present on the biological material, thereby forming two or more amide bonds and covalently crosslinking the biological material.

Suitably, the crosslinking of the biological material (e.g. collagen) by the compositions of the present invention may be enhanced by the inclusion of one or more peptide coupling reagents into the composition of the present invention. Any suitable peptide coupling reagent capable of enhancing the reaction between the carboxy or anhydride groups of the cross-linker and the amine groups of the biological material may be used.

In an embodiment, the peptide coupling reagent is non-toxic, water soluble and/or biocompatible in the amounts required for therapeutic administration.

In another embodiment, the concentration of the peptide coupling reagent in the pharmaceutical formulation of the present invention is between 0 and 2.0 $molL^{-1}$ Suitably, the concentration of the peptide coupling reagent in the pharmaceutical formulation of the present invention is between 0 and 1.0 $molL^{-1}$. More suitably, the concentration of the peptide coupling reagent in the pharmaceutical formulation of the present invention is between 0 and 0.5 $molL^{-1}$. Yet more suitably, the concentration of the peptide coupling reagent in the pharmaceutical formulation of the present invention is between 0 and 0.4 $molL^{-1}$. Most suitably, the concentration of the peptide coupling reagent in the pharmaceutical formulation of the present invention is between 0 and 0.25 $molL^{-1}$.

In another embodiment, the peptide coupling reagent is a carbodimide based coupling reagent. Suitably, the peptide coupling reagent is selected from N,N'-dicyclohexylcarbodiimide (DCC), N,N'-diisopropylcarbodiimide (DIC), 1-ethyl-3-(3-dimethylaminopropyl)carbodiimide (EDCI), N-cyclohexyl-N'-isopropylcarbodiimide (CIC) or N,N'-dicyclopentylcarbodiimide (CPC). More suitably, the coupling reagent is selected from N,N'-dicyclohexylcarbodiimide (DCC), N,N'-diisopropylcarbodiimide (DIC) or 1-ethyl-3-(3-dimethylaminopropyl)carbodiimide (EDCI). Most suitably, the coupling reagent is 1-ethyl-3-(3-dimethylaminopropyl)carbodiimide (EDCI).

Additional activating agents such as, for example, hydroxybenzotriazole (HOBt), N-hydroxy 2-phenyl benzimidazole (HOBI), 1-hydroxy-7-azabenzotriazole (HOAt), N-hydroxysuccinimide (NHS), N-hydroxysulfosuccinimide (Sulfo-NHS), 4-dimethylaminopyridine (DMAP) and ethyl cyano(hydroxyimino)acetate (Oxyma Pure®) may also be used together with the peptide coupling reagent defined hereinabove, to further enhance reactivity between the cross-linkers of the present invention and the amino functionality of the biological material (e.g. collagen).

In an embodiment, the activating agent is N-hydroxysuccinimde (NHS), N-hydroxysulfosuccinimide (Sulfo-NHS) or ethyl cyano(hydroxyimino)acetate (Oxyma Pure®). Suitably, the activating agent is N-hydroxysuccinimde (NHS).

The activating agent may be present in any suitable concentration. In an embodiment, the activating agent is present in a concentration of between 0 and 2.0 $molL^{-1}$ Suitably, the concentration of the activating agent in the pharmaceutical formulation of the present invention is between 0 and 1.0 $molL^{-1}$. More suitably, the concentration of the activating agent in the pharmaceutical formulation of the present invention is between 0 and 0.5 molL$^{-1}$. Yet more suitably, the concentration of the activating agent in the pharmaceutical formulation of the present invention is between 0 and 0.4 molL$^{-1}$. Most suitably, the concentration of the activating agent in the pharmaceutical formulation of the present invention is between 0 and 0.25 molL$^{-1}$.

In another embodiment, the molar ratio of cross-linker: peptide coupling reagent:activating agent of the present invention is 1:1:1.

In a particular embodiment, the composition of the present invention comprises both a peptide coupling reagent and an activating agent. Suitably, the peptide coupling reagent is 1-ethyl-3-(3-dimethylaminopropyl)carbodiimide (EDCI), optionally in an amount of 0 and 0.5 molL$^{-1}$, and the activating agent is N-hydroxysuccinimide (NHS), optionally in the amount of 0 and 0.5 molL$^{-1}$.

In an embodiment, both a peptide coupling reagent and an activating agent are used to enhance the cross-linking reaction with the biological material (e.g. collagen).

The peptide coupling reagent and any activating agent present, may be mixed with the cross-linker either prior to, during or following the administration of the crosslinker to the eye.

In an embodiment, the peptide coupling reagent and any activating agent used are incorporated into the pharmaceutical compositions defined herein.

In an alternative embodiment, the peptide coupling agent and any activating agent are present in a separate aqueous formulation that is mixed with the pharmaceutical compositing comprising the cross-linker as defined herein either prior to, during or following the administration of the pharmaceutical composition to the eye. In such cases, the separate aqueous formulation comprising the peptide coupling reagent and any activating agent will need to be suitable for application to the eye (e.g. have a pH within the ranges defined hereinbefore).

Additional Excipients

It will be appreciated that the pharmaceutical compositions of the present invention may comprise additional pharmaceutical excipients. Additional excipients may be included to improve various properties of the formulation, such as, for example, formulation stability, biocompatibility and administrability. A person skilled in the art will be able to select suitable excipients to include based on conventional knowledge in the formulation field.

A non-limiting list of possible additional excipients that may be added to the pharmaceutical compositions of the present invention include: pH modifiers, surfactants, viscosity modifiers, tonicity agents, sterilising agents, preservatives, lubricants and solubility enhancers.

In an embodiment, the pharmaceutical compositions may also comprise one or more additional therapeutic agents, such as, for example, antibiotics, steroids, anaesthetics and/or antihistamines.

In a particular embodiment, the pharmaceutical compositions of the present invention comprise an anaesthetic. Suitably, the anaesthetic is selected from proxymetacaine HCl (also known as proparacaine), oxybuprocaine hydrochloride, amethocaine hydrochloride or lidocaine hydrochloride. More suitably, the anaesthetic is proxymetacaine HCl.

Particular Embodiments

In an embodiment, the pharmaceutical compositions of the present invention comprise:

a non-toxic, water soluble cross-linker as defined herein;
a buffer to maintain the composition in the pH range 6 to 8;
an aqueous vehicle; and
optionally one or more peptide coupling reagents.

In an embodiment, the pharmaceutical compositions of the present invention comprise:

a non-toxic, water soluble cross-linker of formula (I) or (II), as defined herein;
a buffer to maintain the composition in the pH range 6 to 8;
an aqueous vehicle; and
optionally one or more peptide coupling reagents.

In an embodiment, the pharmaceutical compositions of the present invention comprise:

a non-toxic, water soluble cross-linker of formula (I), as defined herein;
a buffer to maintain the composition in the pH range 6 to 8;
an aqueous vehicle; and
optionally one or more peptide coupling reagents.

In an embodiment, the pharmaceutical compositions of the present invention comprise:

a non-toxic, water soluble cross-linker selected from bis(succinimidyl)penta(ethylene glycol), sebacic, azelaic, suberic, pimelic, adipic, glutaric, succinic acid, malonic or oxalic acid;
a buffer to maintain the composition in the pH range 6 to 8;
an aqueous vehicle; and
optionally one or more peptide coupling reagents.

In an embodiment, the pharmaceutical compositions of the present invention comprise:

a non-toxic, water soluble cross-linker selected from sebacic, azelaic, suberic, pimelic, adipic, glutaric, succinic acid, malonic or oxalic acid;
a buffer to maintain the composition in the pH range 6 to 8;
an aqueous vehicle; and
optionally one or more peptide coupling reagents.

In an embodiment, the pharmaceutical compositions of the present invention comprise:

a non-toxic, water soluble cross-linker selected from bis(succinimidyl)penta(ethylene glycol), sebacic, azelaic, suberic, pimelic or adipic acid;
a buffer to maintain the composition in the pH range 6 to 7.5;
an aqueous vehicle; and
optionally one or more carbodiimide peptide coupling reagents and an activating agent (e.g. N-hydroxysuccinimide).

In an embodiment, the pharmaceutical compositions of the present invention comprise:

a non-toxic, water soluble cross-linker selected from sebacic, azelaic, suberic, pimelic or adipic acid;
a buffer to maintain the composition in the pH range 6 to 7.5;
an aqueous vehicle; and
optionally one or more carbodiimide peptide coupling reagents and an activating agent (e.g. N-hydroxysuccinimide).

Therapeutic Uses and Applications

The pharmaceutical compositions of the present invention are particularly suited to the treatment of collagenic eye disorders. Once administered, the pharmaceutical compositions deliver the cross-linker to the eye, thereby initiating the crosslinking of collagen within the eye and restoring structural integrity to the eye.

Thus, the present invention provides a pharmaceutical composition as defined herein for use in the treatment of a collagenic eye disorder.

In another aspect, the present invention provides a method of treating a collagenic eye disorder, said method comprising administering to a human or animal subject in need of such treatment a therapeutically effective amount of a pharmaceutical composition as defined herein.

In yet another aspect, the present invention provides a non-toxic, water soluble cross-linker comprising two or more carboxyl groups and/or one or more anhydride groups, or a pharmaceutically acceptable salt thereof, for use in the treatment of a collagenic eye disorder. Suitably, the cross-linker is administered in combination with one or more peptide coupling reagents.

In yet another aspect, the present invention provides a method of treating a collegenic eye disorder, said method comprising administering to a human or animal subject in need of such treatment a therapeutically effective amount of a non-toxic, water soluble cross-linker comprising two or more carboxyl groups and/or one or more anhydride groups, or a pharmaceutically acceptable salt thereof. Suitably, the cross-linker is administered in combination with one or more peptide coupling reagents.

The cross-linker and pharmaceutical compositions defined herein may be used to treat and collagenic eye disorder. Collagenic eye disorders are any eye disorder or medical application that is associated with the weakening, degradation and/or damage to collagen in the eye. The term encompasses the weakening, degradation and/or damage to all parts of the eye, such as, for example, the cornea and the sclera.

Collagenic eye disorders that can be treated with the cross-linker and pharmaceutical compositions defined herein include:

1. corneal ectasia, including:
   (i) non-inflammatory corneal ectasia—e.g. keratoconus, keratoglobus, pellucid marginal degeneration;
   (ii) inflammatory corneal ectasia;
   (iii) iatrogenic corneal ectasia (keratectasia)—e.g. following laser refractive procedures/refractive surgery (LASIK, LASEK, PRK);
   (iv) myopia (i.e. crosslinking of collagen in sclera to treat progressive myopia);
2. inflammation in the eye*, including:
   * by reducing/inhibiting inflammation by destroying inflammatory cells and making the tissue more resistant to digestion; for example, stopping inflammatory mediated cellular damage and enzymatic destruction of collagen or proteoglycans and treatment of corneal or scleral stromal ulceration and melts.
   (i) treatment of the cornea resulting from infective, traumatic (chemical, physical, thermal, surgical) or immune-mediated (including vasculitic) corneal disease;
   (ii) sclera resulting from infective, traumatic (chemical, physical, thermal, surgical) or immune-mediated (including vasculitic) scleral disease, including scleromalacia perforans;
   ** as a result of connective tissue disease, such as rheumatoid arthritis (RA), Sjogren syndrome, Mooren ulcer, or any systemic vasculitic disorder/collagen vascular disease (eg, systemic lupus erythematosus [SLE], Wegener granulomatosis, polyarteritis nodosa).
3. re-shaping of the cornea, including:
   (i) reshaping the donor cornea for transplantation***
   *** for better tissue healing and refractive outcomes.
   (ii) stabilising corneal shape following refractive surgical procedures;
4. corneal swelling due corneal oedema (e.g. bullous keratopathy, Fuchs Endothelial Dystrophy, Congenital Hereditary Endothelial Dystrophy, hydrops of the cornea in keratoconus)
5. mechanically strengthening a weakened sclera (e.g. (i) for the treatment of myopia—crosslinking of collagen in sclera to treat progressive myopia; (ii) glaucoma—scleral cross-linking to alter biomechanical properties of the optic nerve head and lamina cribrosa)

The pharmaceutical compositions of the present invention may be used on their own as the sole therapy. Alternatively, the compositions may be administered as part of a combination therapy with one or more other eye treatments. Such conjoint treatment may be achieved by way of the simultaneous, sequential or separate administration of the individual components of the treatment.

By way of example, collagenic eye disorders may result in a number of other undesirable symptoms to the patient, such as, for example, pain, infection, dryness and discomfort. Accordingly, the pharmaceutical compositions of the present invention may be used in combination with one or more additional medicaments or additives, such as, for example, hydrating agents, antibiotics, steroids, anaesthetics and antihistamines.

The pharmaceutical compositions of the present invention may be presented as typical formulations for administration to the eye, e.g. eye drops (including viscous eye drops), eye sprays, eye washes or eye creams/ointments.

Administration Devices

The pharmaceutical compositions of the present invention may be incorporated into a suitable device to deliver a dose of the composition to the eye during use. Any suitable device known in the art may be used, such as, for example, a conventional eye drop bottle.

In embodiments where the cross-linker is separate from the peptide coupling agent and/or any activating agent that is used, it may be desirable to provide separate devices for delivering each component to the eye separately, e.g. separate containers that enable the respective components to be mixed following application to the eye. Alternatively, it might be desirable to provide a single device having a first compartment that comprises the pharmaceutical composition comprising the cross-linker as defined herein, and a second compartment that comprises the peptide coupling reagent and/or activating agent.

It is generally preferred that the cross-linker, peptide coupling reagent and any activating agent that is used, are mixed together prior to administration to the eye.

Thus, in one aspect, the present invention provides a device for administering a pharmaceutical composition as defined herein to the eye, the device comprising:
(i) a first compartment comprising a pharmaceutical composition as defined herein;
(ii) a second compartment comprising one or more peptide coupling agents dissolved in a suitable pharmaceutically acceptable vehicle;
wherein the device is configured to mix at least a proportion of the contents of the first and second compartments prior to or during dispensing to the eye.

The device may be configured such that the contents (or a proportion thereof) of the first and second compartments can be mixed together and then administered to the eye. Alternatively, the device may be configured such that the contents (or a proportion thereof) of the first and second compartments mix as a dose of the pharmaceutical composting from the first compartment is administered.

DETAILED DESCRIPTION OF THE DRAWINGS

The present invention is further defined with reference to the accompanying figures, where:

EXAMPLES

Figure 1:
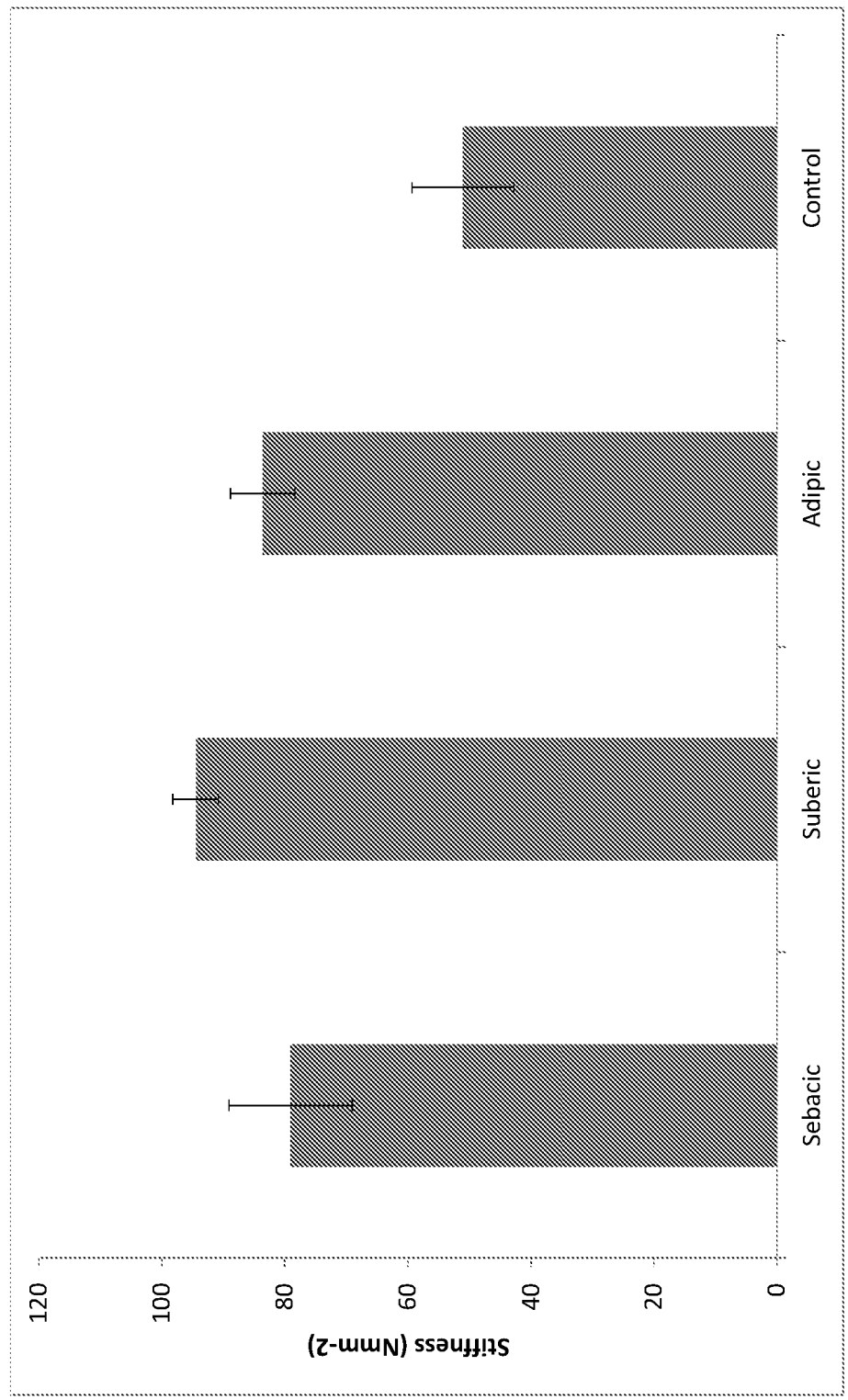
FIG. 1 illustrates the mean stiffness (±sd, n=3) for control untreated pig cornea compared with diacid treated corneas.

Abbreviations
BS(PEG)$_5$ Bis(succinimidyl)penta(ethylene glycol)
DAPI 4',6-diamidino-2-phenylindole
DMAE Dimethylethanolamine
DMEM Dulbecco's Modified Eagle's Medium
EDCI 1-Ethyl-3-(3-dimethylaminopropyl)carbodiimide
FCS Fetal Calf Serum
HCE Human Corneal Epithelial
NBF Neutral Buffered Formalin
NHS N-Hydroxysuccinimide
PBS Phosphate Buffer Saline
Materials and Methods
Preparation of the Eyes Pig eyes were collected from the abattoir on the day of slaughter. They were brought to the laboratory and any remaining soft tissue was carefully dissected away leaving just globe and the small section of optic nerve. These were washed 3 times in PBS. A drop of fluorescein dye (1% diluted 1:10 in PBS) was applied to the cornea of each eye to evaluate the integrity of the corneal epithelium (as used in the clinic). The globes were then washed again in PBS 3 times.

The globes were mounted individually on Perspex rings and placed corneal side down in 6-well cell culture plates. This ensured that the eyes were balanced stably and that the corneal surface was exposed in a controlled manner to the cross-linking solution.
Preparation of the Solutions
25 ml of Solutions Dissolve 575 mg of NHS and 775 mg of EDCI in 22.5 ml of PBS. Dissolve 500 mg Sebacic acid (decanedioic acid) or 435 mg of Suberic acid (octanedioic acid) or 365 mg of Adipic acid (hexanedioic acid) in 2.5 ml of PBS. Add each diacid solution to 22.5 ml of NHS/EDCI solution. This solution had an excess of EDCI and was used for Experiment 1 below.

Experiments 2 and 3 used a Molar ratio of 1:1:1 of suberic:NHS:EDCI using 319 mg NHS, 430 mg EDCI and 241 mg suberic acid. NHS/EDCI dissolved first in 7.5 ml PBS and suberic acid dissolved in 7.5 ml PBS with the addition of 500 ul DMAE to aid solubility. The two solution were added to each other and made up to 15 ml if necessary.
Experiments to Treat Eyes
Experiment 1

Add diacid/NHS/EDCI solution (4-5 ml) to 3 eyes for each diacid and add PBS (4-5 ml) to 3 eyes as control. Incubate for 30 minutes at 37° C. After 30 minutes, wash off solution with PBS (5 times).
Experiment 2

Add suberic acid/NHS/EDCI solution (4-5 ml) to 3 eyes and add PBS (4-5 ml) to 3 eyes as control. Incubate 3 eyes for each of 7.5, 15, 30 and 60 minutes at 37° C. After each time period, wash off solution with PBS (5 times).

Experiment 3

Add suberic acid/NHS/EDCI solution that had been adjusted to pH 7 using NaOH/HCl as required (4-5 ml) to 3 eyes and add PBS (4-5 ml) to 3 eyes as control.

Post Treatment Testing

Add fluorescein dye (as above) to each eye to check the integrity of the epithelium after treatment.

Carefully cut open the eyes around the equator. Punch a 'dogbone' tensile test specimen (gauge length 10 mm, width 2 mm) from each cornea. Measure the width and thickness of each specimen. Conduct a tensile test on each sample using a Linkam TST350 using a 200N load cell and a strain rate of 100 μms$^{-1}$.

To Evaluate Cytotoxicity of the Suberic Acid/NHS/EDCI Solution

Human corneal epithelial cell line (HCE-T cells) was cultured in DMEM/F12HAM (10% FCS, 1 aliquot penstrep/fungisone) at a density of 100,000 cells/well, and 80,000 cells/well on a 24 well plate in triplicate. Cells were allowed to grow to confluence for 7 days in an incubator at 37° C. and 5% $CO_2$. At this point the media was removed and the cells washed with PBS 2 times. 1 ml of suberic/NHS/EDCI solution (not pH neutralised) was added to each test well and incubated for 15 minutes. Following incubation the solution was removed and the cells washed with PBS 3 times. The cells were fixed with NBF (10%) at 10 minutes at room temperature, washed with PBS, permeabilised with Triton-X (1%), washed with PBS and stained with DAPI then phalloidin (5 minutes each at room temperature in the dark). Plates were stored in the dark in the fridge (4° C.) under PBS with 1 aliquot penstrep/fungisone) for a week until they were imaged under fluorescent microscopy.

Crosslinking with Individual Moieties

Since the cross-linking chemistry is based on EDCI/NHS mediated chemistry, the individual active moieties being used (EDCI and NHS) in the treatment solution are chemically able to crosslink proteins. The ability at which the individual chemicals are able to increase the biomechanical property of the cornea was assessed. Corneas were prepared, the masses of all the chemicals were measured out, and the corneas were treated as described above. The following treatment solutions were set up:

2:1 EDCI/suberic only
2:1 NHS/suberic only
1:1:1 EDCI/NHS/suberic
Control (PBS)

All corneas were treated for 15 minutes at 37° C. The treated corneas were prepared as described above and the tensile tested as described above.

Crosslinking with Treatment Solutions Set to pH 7

The following treatment solutions were set up and the pH of the solutions set to pH 7:

2:1 EDCI/suberic only
2:1 NHS/suberic only
1:1:1 EDCI/NHS/suberic
Control (PBS)

All corneas were treated for 15 minutes at 37° C. The treated corneas were prepared as described above and then tensile tested as described above.

Measuring pH Change Over Time

The pH of the following treatment solutions were measured over time for 2 hours with a digital pH-meter:

Original (molar ratios as used in "Experiment 1")
1:1:1 EDCI/NHS/Suberic acid
2:1 NHS/Suberic acid
2:1 EDCI/Suberic acid The solutions were mixed and measured at the following times:

Immediately after mixing
15 minutes after mixing
30 minutes after mixing
60 minutes after mixing
120 minutes after mixing Unwanted Side Reactions and Precipitate Formation If EDCI and NHS are mixed together and left to stand for long periods of time, heat and $CO_2$ gas bubbles are released, suggesting that the two compounds are decomposing. It is therefore advisable to mix the treatment solutions immediately before crosslinking is required.

Within the 15 minutes treatment time a precipitate forms in the 1:1:1 EDCI/NHS/suberic acid treatment solution. To allow a more complete analysis of the treatment solution, aliquots of the mixture were taken of the individual moieties before mixing and the solution immediately after mixing and cast on to glass slides to dry at 37° C. for FTIR analysis. The precipitate from the 1:1:1 treatment solution was allowed the settle overnight undisturbed after mixing together. The precipitate was isolated on filter paper and allowed to dry overnight at 37° C., and an aliquot of the filtrate was cast on to a glass slide to allow to dry overnight at 37° C. before FTIR analysis. The dried mass of the precipitate was measured and compared to the theoretical mass of the precipitate that may form. Corneas were analysed by FT-IR to ascertain change in chemistry.

Solubilised NHS-ester and BS(PEG)$_5$ Corneal Crosslinking

NHS-ester (made from NHS and suberic acid) as solubilised in neat DMSO, and BS(PEG)$_5$ was made up to a stock using the standard instructions using DMSO. This stock was made up to a working solution as 60 μl BS(PEG)$_5$ in 15 ml PBS for crosslinking. Eyes were treated for 15 minutes at 37° C., tensile tested as described above, and the corneas analysed by FT-IR to ascertain change in chemistry.

Critical NHS/EDCI Molar Ratio for Cross-linking

According to a paper by Lai (Int. J. Mol. Sci. 2013, 14, 2036-2055), the critical NHS/EDCI molar ratio should be 0.5 for optimal crosslinking of collagen ex vivo. This was assessed by setting up treatment 1:1:1, 0.5:1:1, and 1:0.5:1 solutions with the NHS/EDCI molar ratios of 1, 2, and 0.5 respectively. The mass of the suberic acid was kept constant, as described in experiments 2 and 3. The NHS/EDCI were added together first and then the suberic acid added afterwards. Corneas were treated and tested as described above.

Enhancing Transepithelial Cross-linking with Anaesthetic

Anaesthetic is routinely used in ophthalmic procedures as an analgesic and to loosen tight junctions in the corneal epithelium to enhance the instilment of riboflavin during routine UV/riboflavin crosslinking procedures. Proxymetacaine HCL 0.5% w/v (also known as proparacaine) was applied to eyes using standard method of administration according to the product characteristics: "deep anaesthesia: instil 1 drop every 5-10 minutes for 5-7 applications", followed by a "period of at least 1 minute . . . before subsequent administration of other topical agents". Eyes were prepared as described hereinabove, with the proxymetacaine applied before application of the 1:1:1 treatment solution as previously described. Eyes were tensile tested as described above.

Comparing UV/Riboflavin Vs 1:1:1 EDCI/NHS/Suberic Acid on Stroma Mechanical Properties For this test the corneas were excised and the epithelium and endothelium were removed by scraping with a scalpel before crosslinking treatment. The following treatments were compared:

UV/Riboflavin
0.1% riboflavin dissolved in PBS
Stroma was mounted onto a mould to maintain curvature and expose epithelial side only. A metal ring was mounted on to the top surface of the stroma to hold riboflavin in position and the ring filled with riboflavin solution for 2×15 minutes. Following this the ring was removed and UV light applied continuously with a drop of riboflavin applied every 3 minutes until crosslinking was complete.
Machine: X-Link corneal crosslinking system
Power: 2.36 mW
Intensity: 3.004 mw/cm$^2$
Time: 30 minutes
Temperature: Standard laboratory temperature
1:1:1 EDCI/NHS/Suberic acid
Control (PBS)

For the 1:1:1 and control treatments, the corneas were dipped face-down into the solutions so they only made contact with the epithelial side of the cornea for 15 minutes at 37° C. Tensile testing was carried out as previously described.

Results

All diacid solutions increased the stiffness of the pig corneas in comparison with control untreated corneas after 30 minutes of incubation (FIG. 1). Treatment with the suberic acid solution exhibited the highest stiffness, with an 84.9% increase in value compared to the untreated control corneas. Sebacic acid and adipic acid solutions were found to increase the stiffness by 54.8% and 63.6% respectively in comparison with untreated controls.

Figure 2:
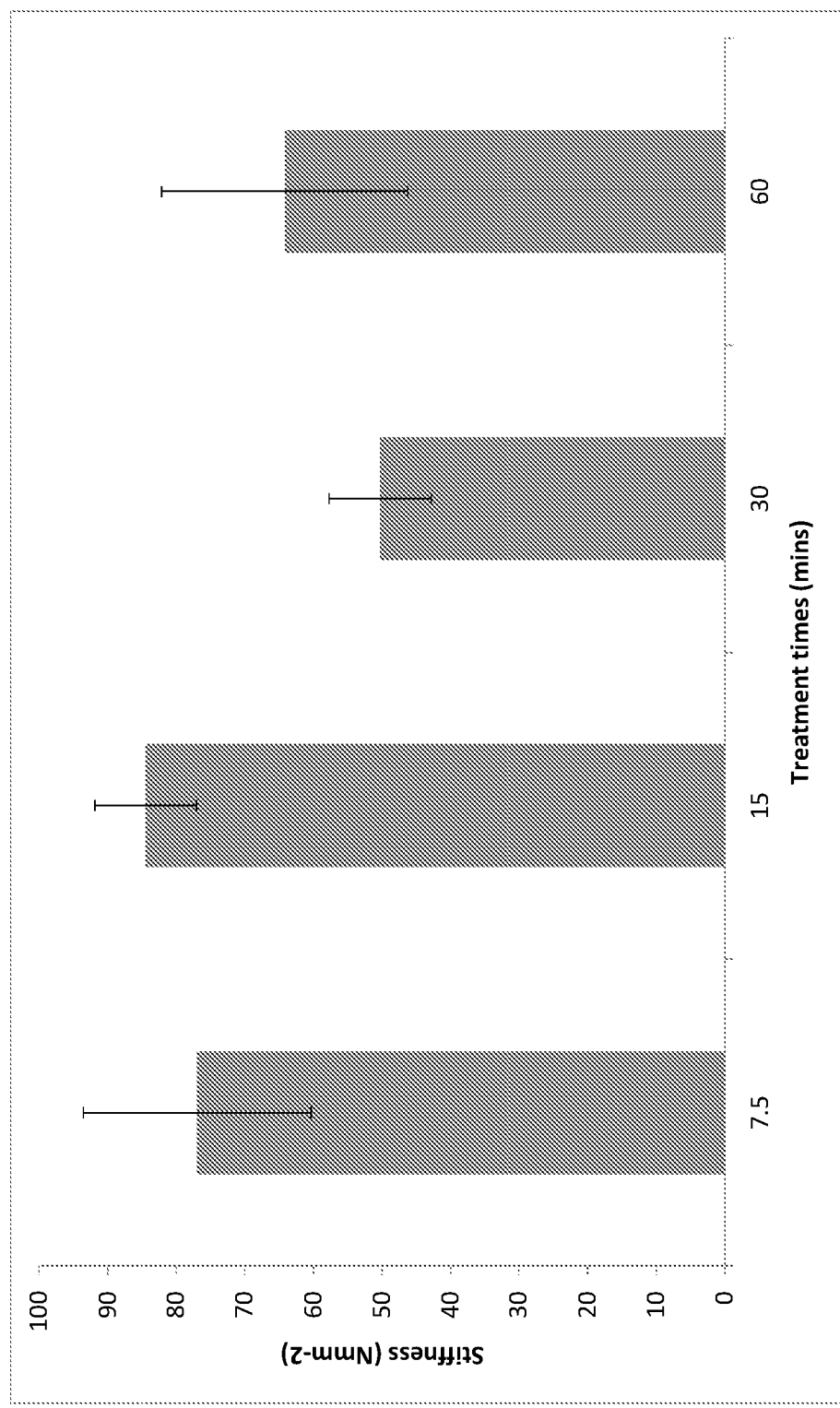
FIG. 2 illustrates the mean stiffness (±sd, n=3) for pig corneas treated with suberic acid/NHS/EDCI for different time periods.

Comparison of treatment time demonstrated that the maximum stiffness for cornea treated with suberic/NHS/EDCI solutions occurred after a 15 minute incubation (FIG. 2). After this time some precipitate was observed suggesting that the reaction was complete.

Neutralisation of the pH of the suberic/NHS/EDCI solution resulted in a slightly reduced increase in stiffness to 53% after a 15 minute treatment in comparison with untreated cornea.

Figure 3:
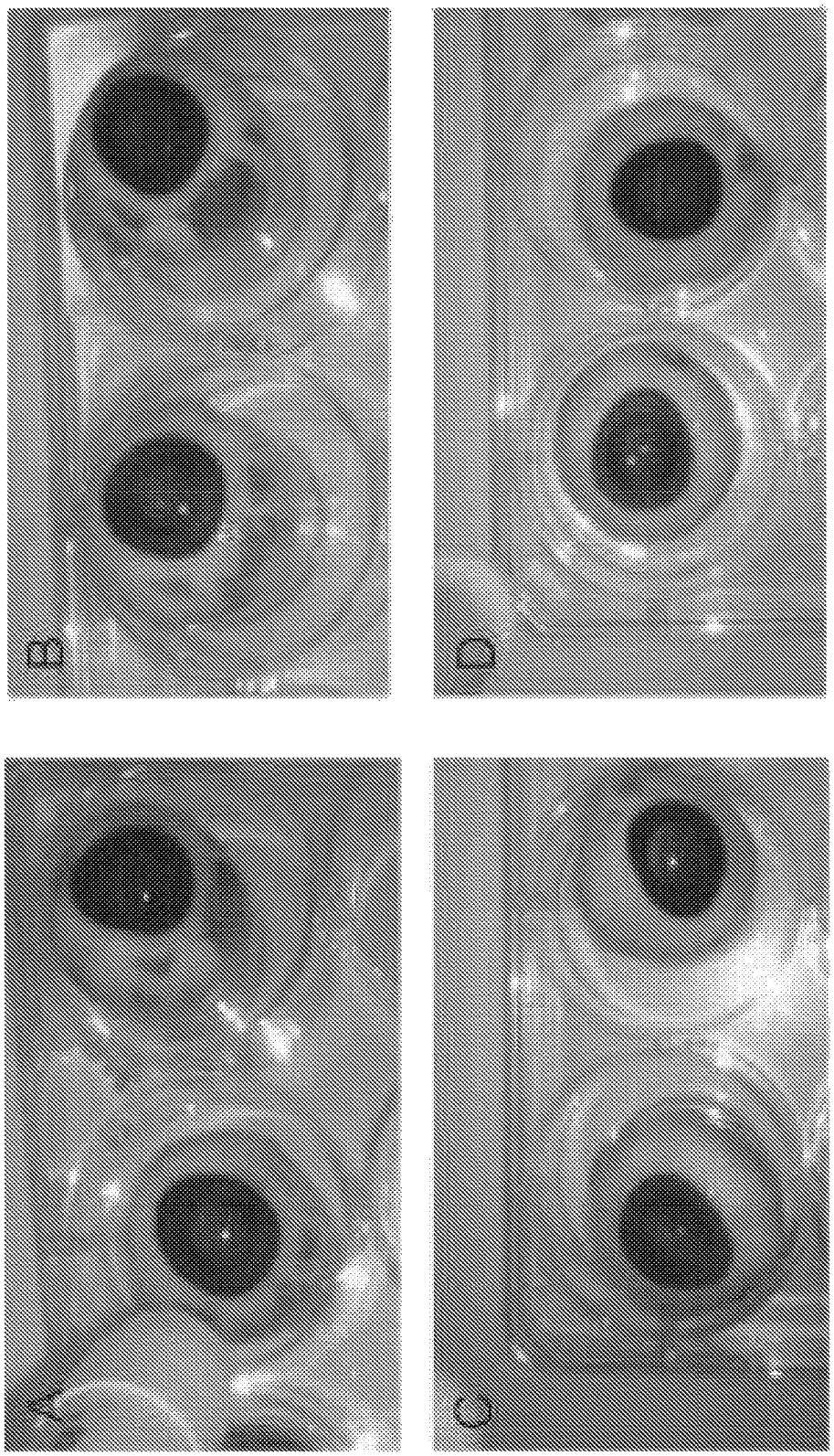
FIG. 3 illustrates pig eye globes with fluorescein dye illuminated with blue light to demonstrate epithelial defects where it fluoresces, wherein A) illustrates the control pre-treatment, B) illustrates the control post-treatment, C) illustrates Suberic acid/NHS/EDCI pre-treatment and D) illustrates Suberic acid/NHS/EDCI post-treatment.

Exposure of the cornea to fluorescein before and after treatment demonstrated no change in the integrity of the corneal epithelium although all epithelial surfaces had small areas of defects most likely due to the slaughtering and eye preparation procedures (FIG. 3).

Figure 4A:
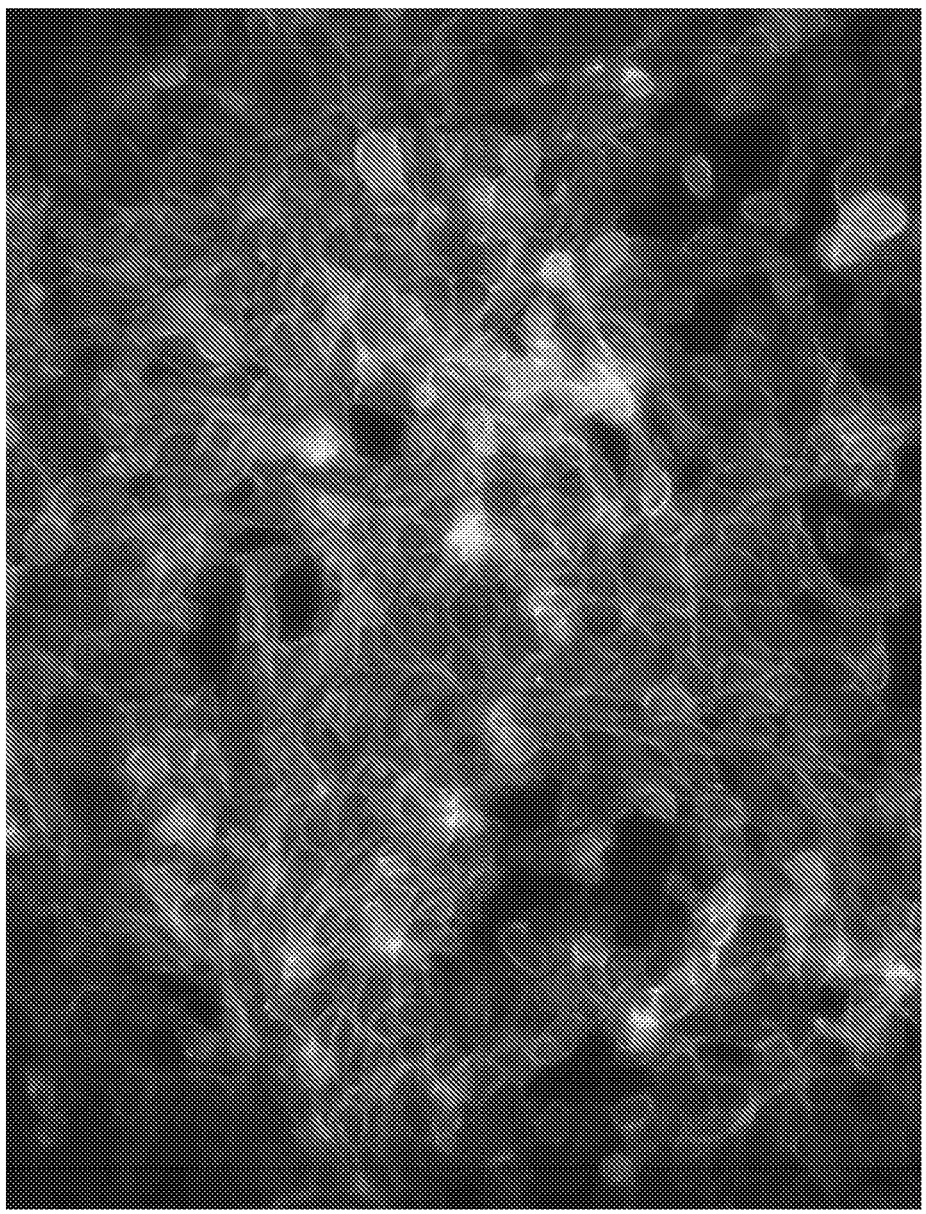
FIG. 4 illustrates photomicrographs of HCE-T cell cultures after 7 days for A) control culture (100000 cell seeding density), B) after treatment with Suberic acid/NHS/EDCI (100000 cell seeding density), C) after treatment with Suberic acid/NHS/EDCI (80000 cell seeding density) stained with DAPI and Phalloidin, scale bar=100 microns.
Figure 4B:
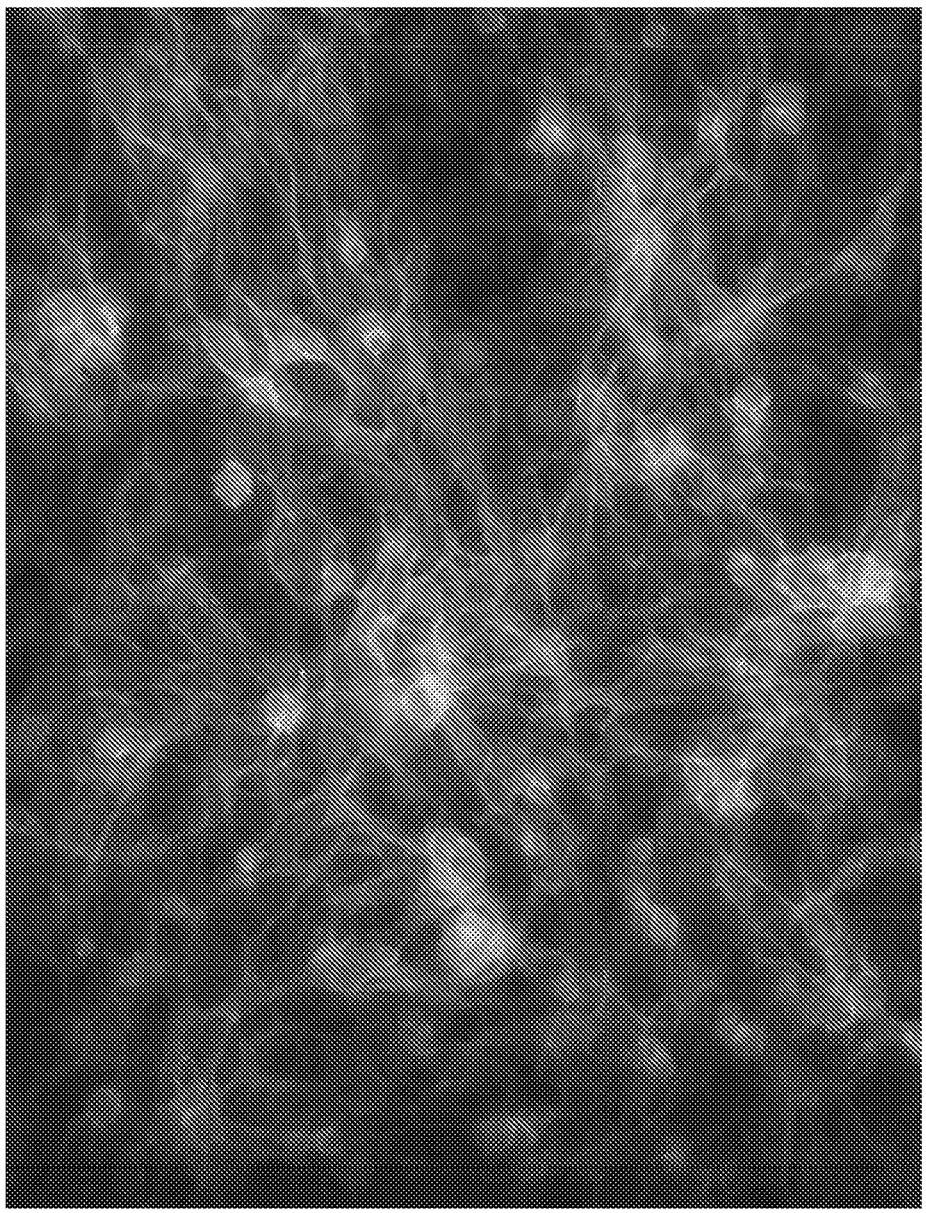
Figure 4C:
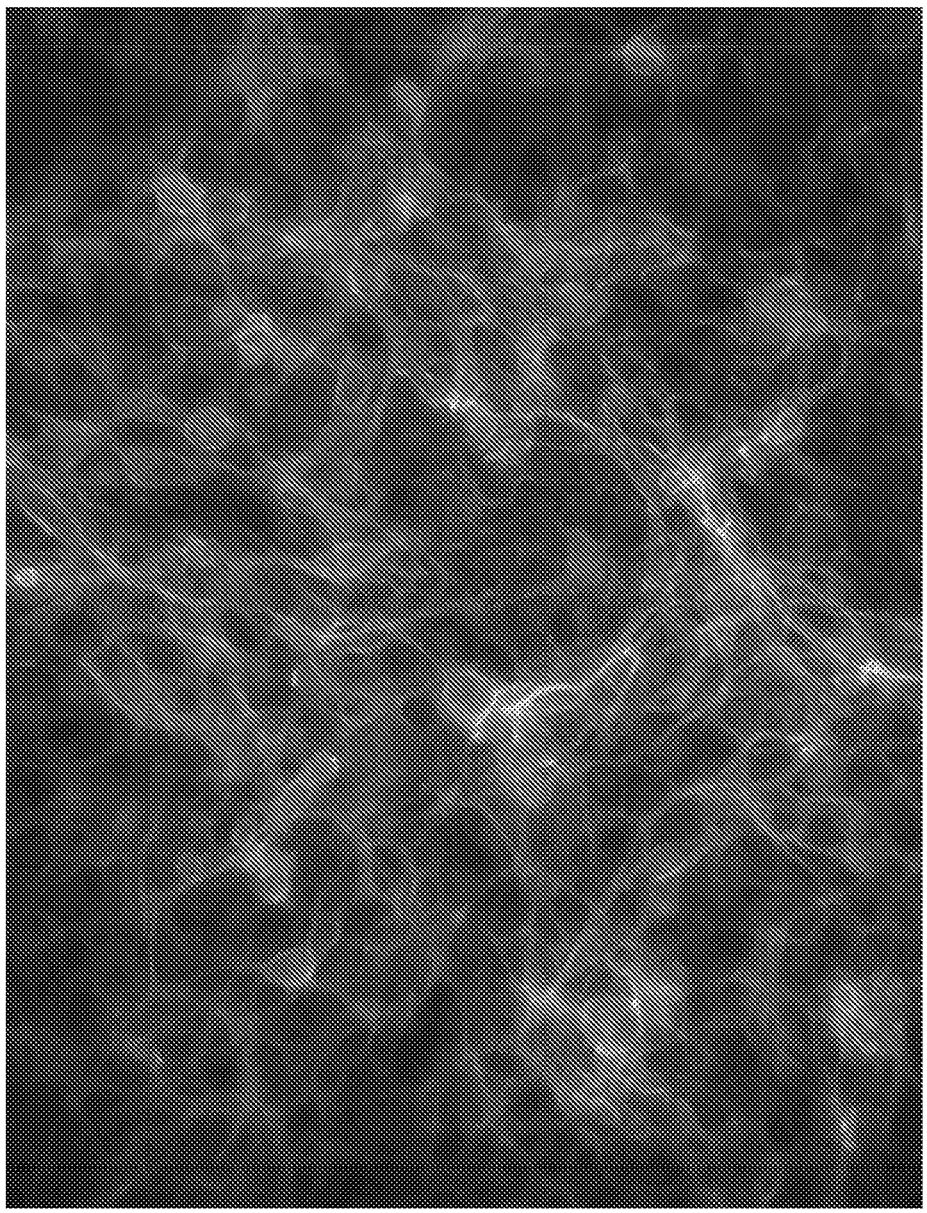

Qualitatively there was no difference between control cultures of HCE-T cells and those treated with the suberic/NHS/EDCI (not pH neutralised) for 15 minutes. Both control and treated cultures appeared to be confluent cultures with the correct 'cobblestone' epithelial morphology (FIG. 4 a, b and c).

Figure 5:
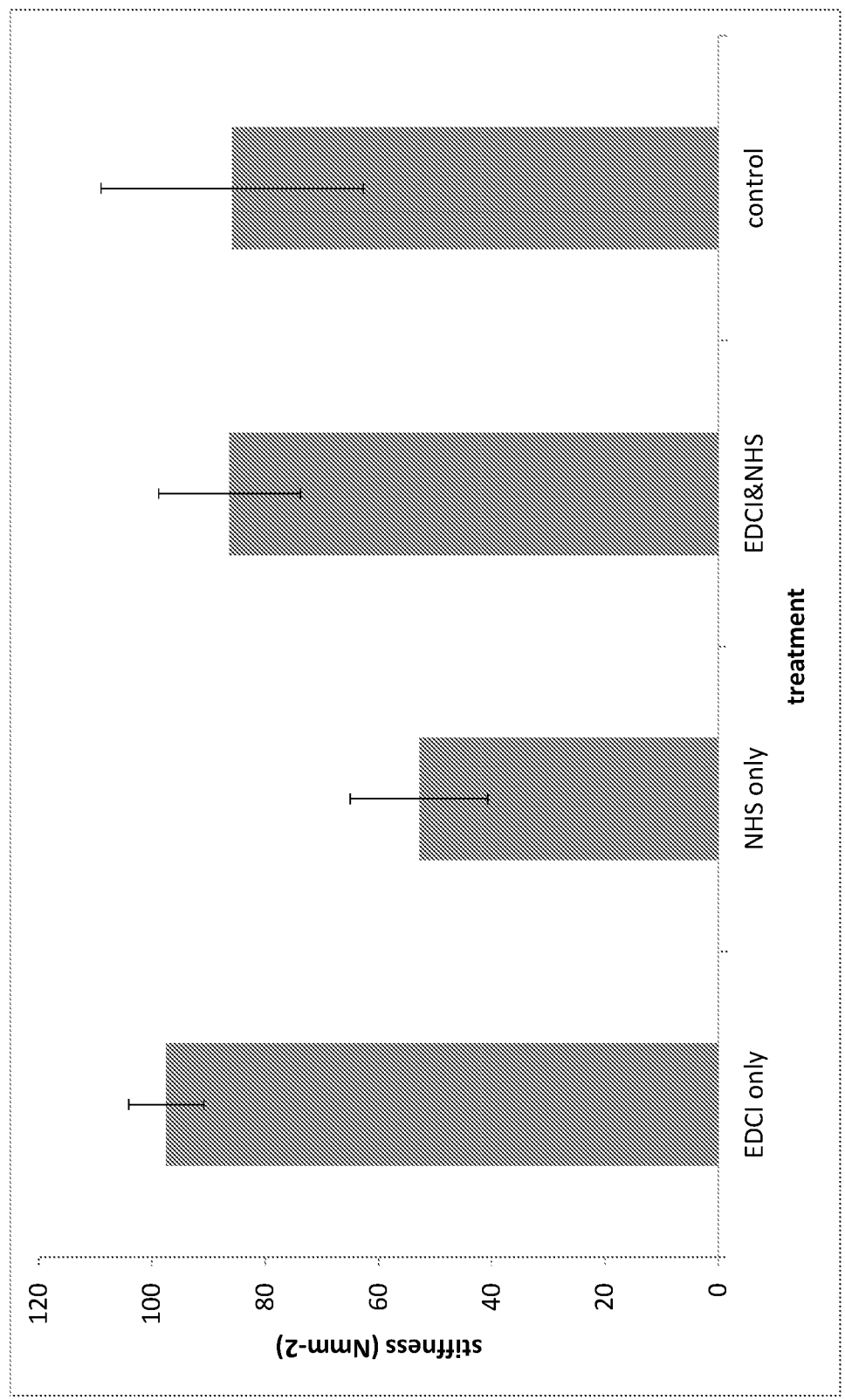
FIG. 5 illustrates the mean stiffness (±sd, n=3) for pig corneas treated with: 2:1 EDCI/suberic acid; 2:1 NHS/suberic acid; 1:1:1 EDCI/NHS/suberic acid; and a control (untreated corneas) for 15 minutes.

Crosslinking with the individual moieties showed there was a marked difference between the EDCI only and NHS only treated cornea (FIG. 5). The EDCI only treated corneas exhibited the highest increase in stiffness.

Figure 6:
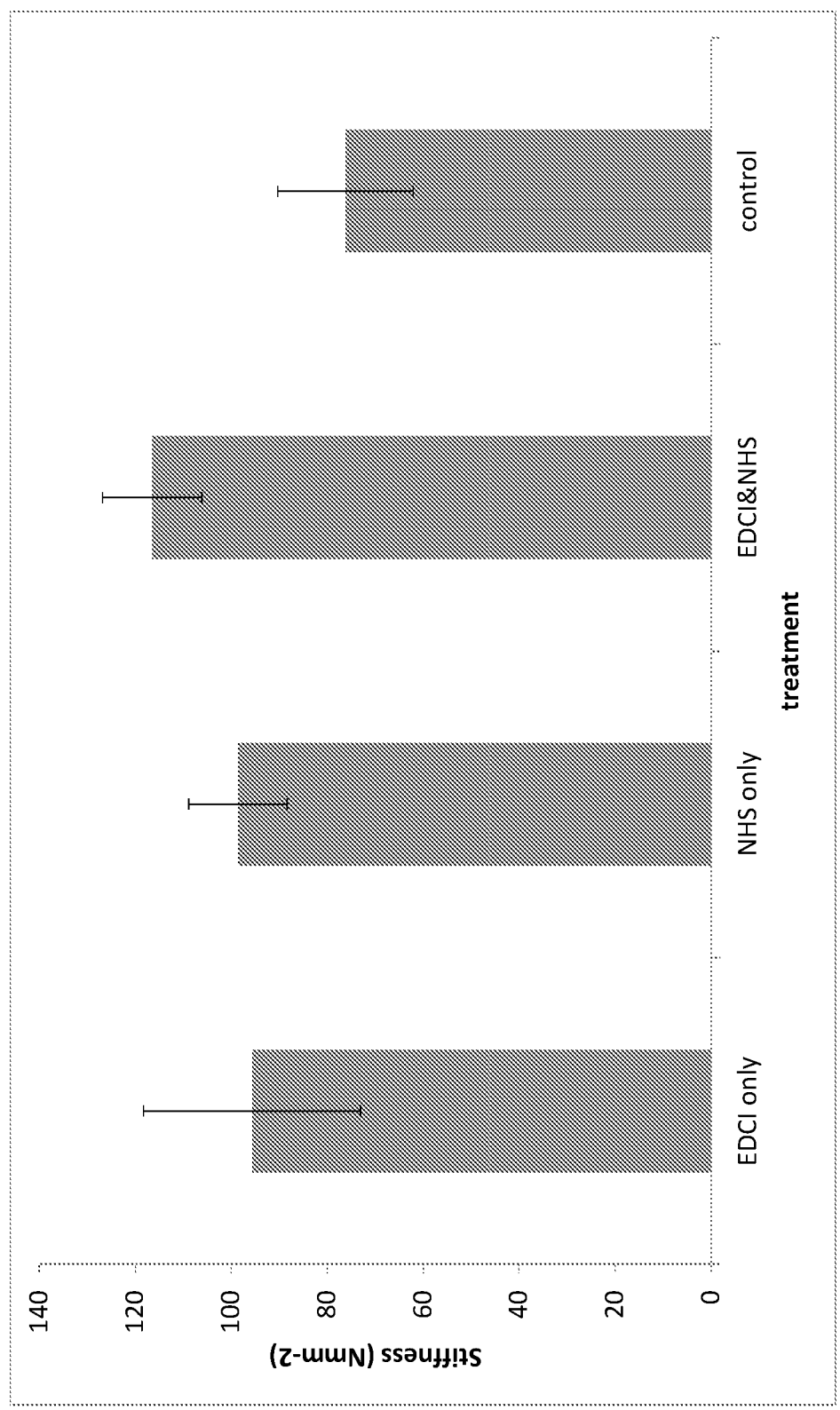
FIG. 6 illustrates the mean stiffness (±sd, n=3) for pig corneas treated with: 2:1 EDCI/suberic acid; 2:1 NHS; 1:1:1 EDCI/NHS/suberic acid; and a control (untreated corneas) for 15 minutes at pH 7.

Neutralisation of the pH of the suberic/NHS/EDCI solution resulted in an increase in stiffness after a 15 minute treatment in comparison with untreated cornea (FIG. 6). In particular the neutralisation of the EDCI only (from around pH 9 to pH 7) resulted in a reduction in the stiffening effect, whereas the neutralisation of the NHS only increased the stiffening effect.

Figure 7:
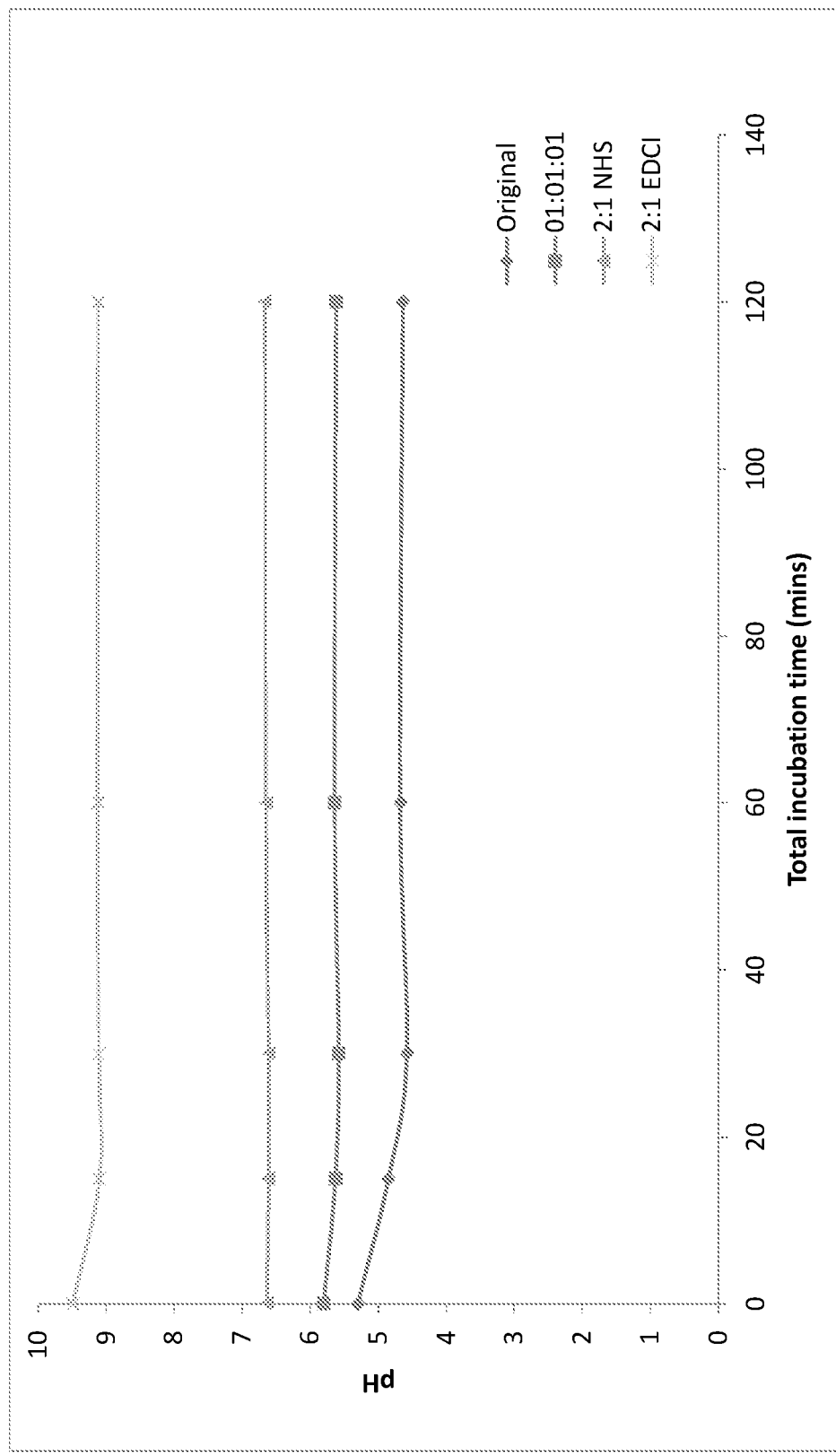
FIG. 7 illustrates the pH values for 1:1:1 EDCI/NHS/suberic acid, 2:1 EDCI/suberic and 2:1 NHS/suberic with an unchanged pH of the reaction conditions.
Figure 8:
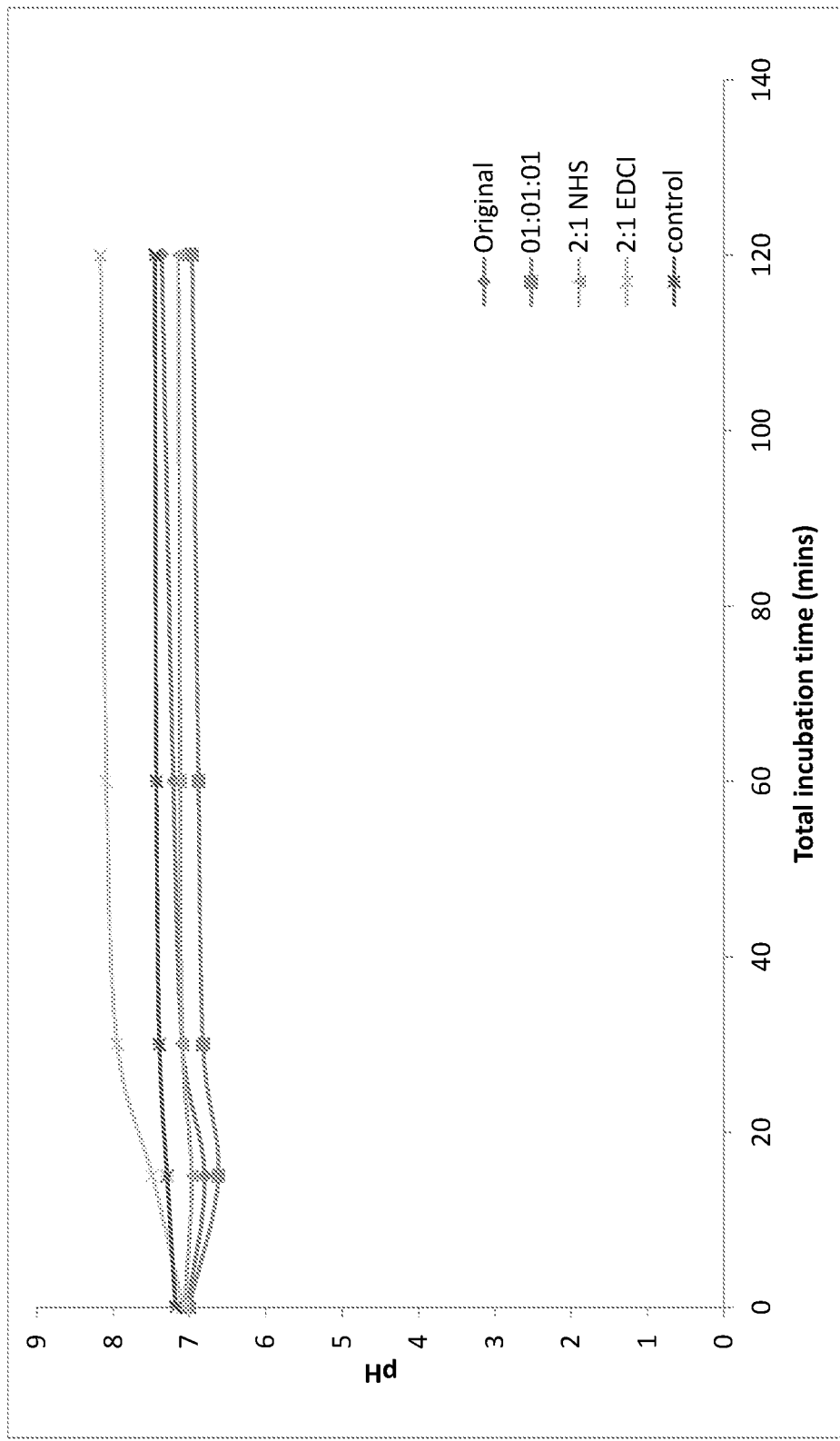
FIG. 8 illustrates the pH values for 1:1:1 EDCI/NHS/suberic acid, 2:1 EDCI/suberic and 2:1 NHS/suberic with a neutralised pH (pH 7).

The pH of the treatment solutions changed with incubation time for both the un-altered pH (FIG. 7) and neutralised pH (FIG. 8). For both conditions, the pH changed most during the first 30 minutes after mixing all solution which suggests that the reactions are most active within this time.

The mechanism for the EDCI/NHS mediated reaction with a carboxylate is currently unknown. A widely accepted mechanism is one proposed by Nakajima and Ikada (*Bioconjugate Chem.*, 1995, 6, 123-1 30), which describes a coupling reaction, in which protons are donated and accepted to create charged moieties. It is these moieties that undergo coupling reactions with the carboxylate group. This can also be supported by the change in pH the reaction solutions undergo.

Figure 9:
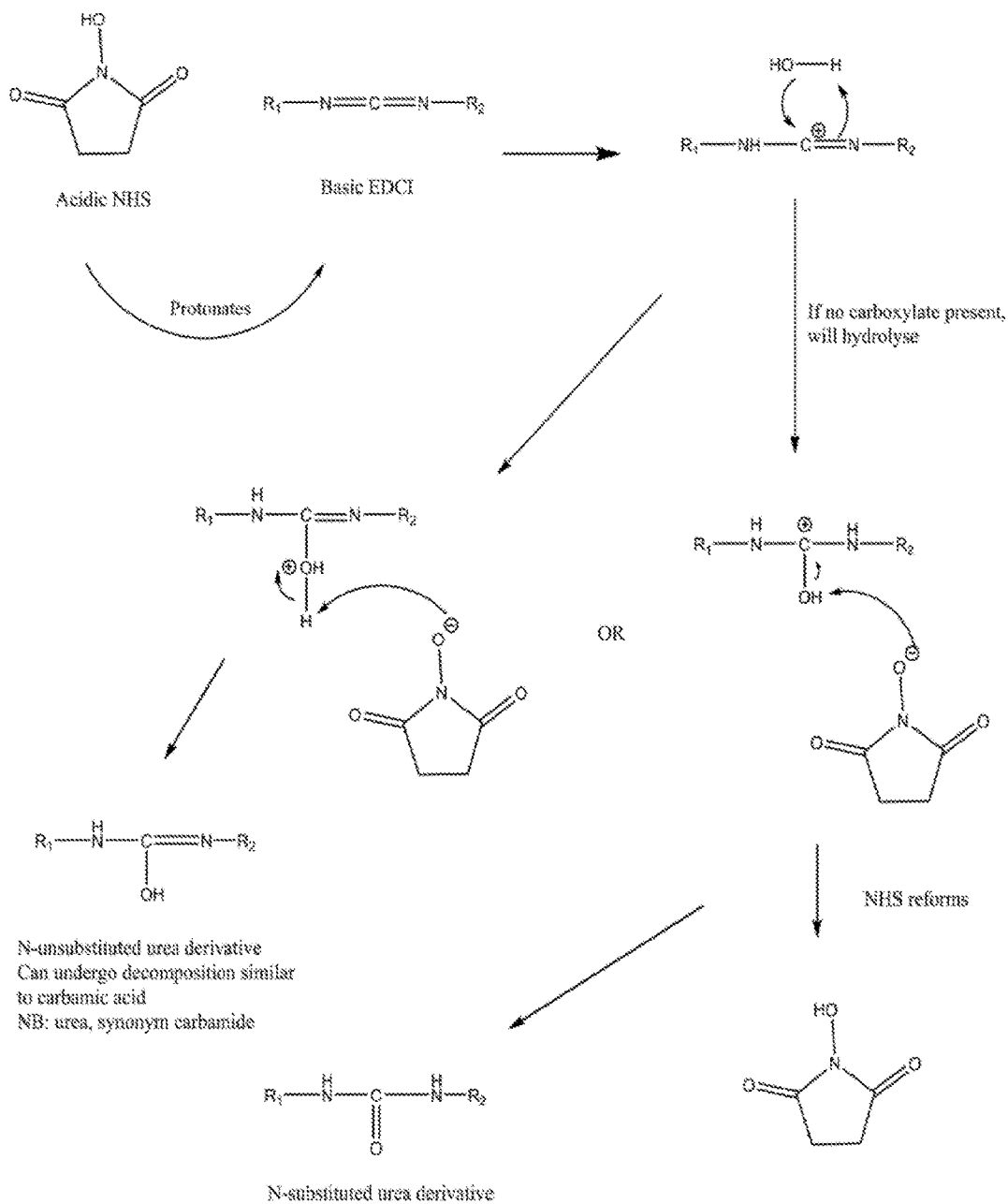
FIG. 9 illustrates the likely mechanism of the unwanted side reactions that may occur between NHS and EDCI in the absence of any carboxylate group.
Figure 10:
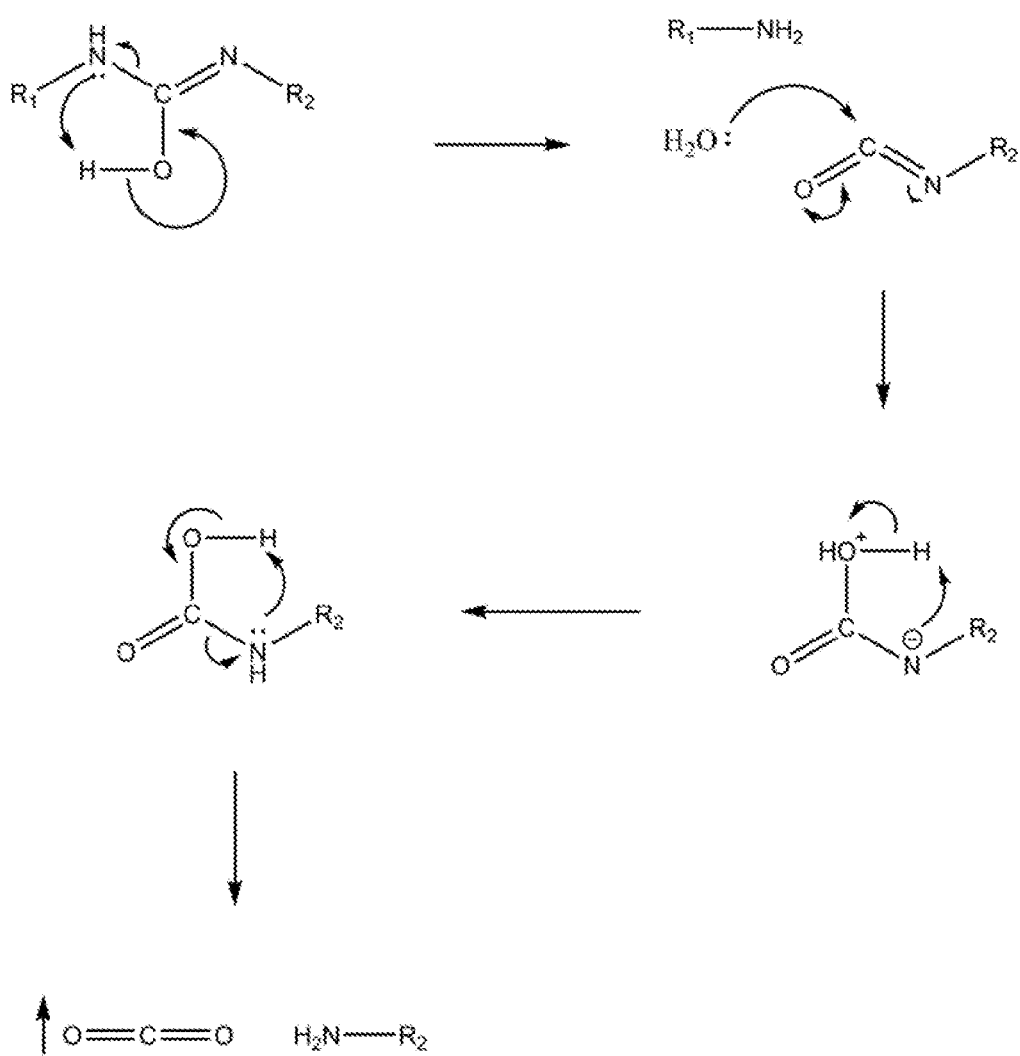
FIG. 10 illustrates the likely mechanism of the decomposition reaction which results in the release of $CO_2$.
Figure 11:
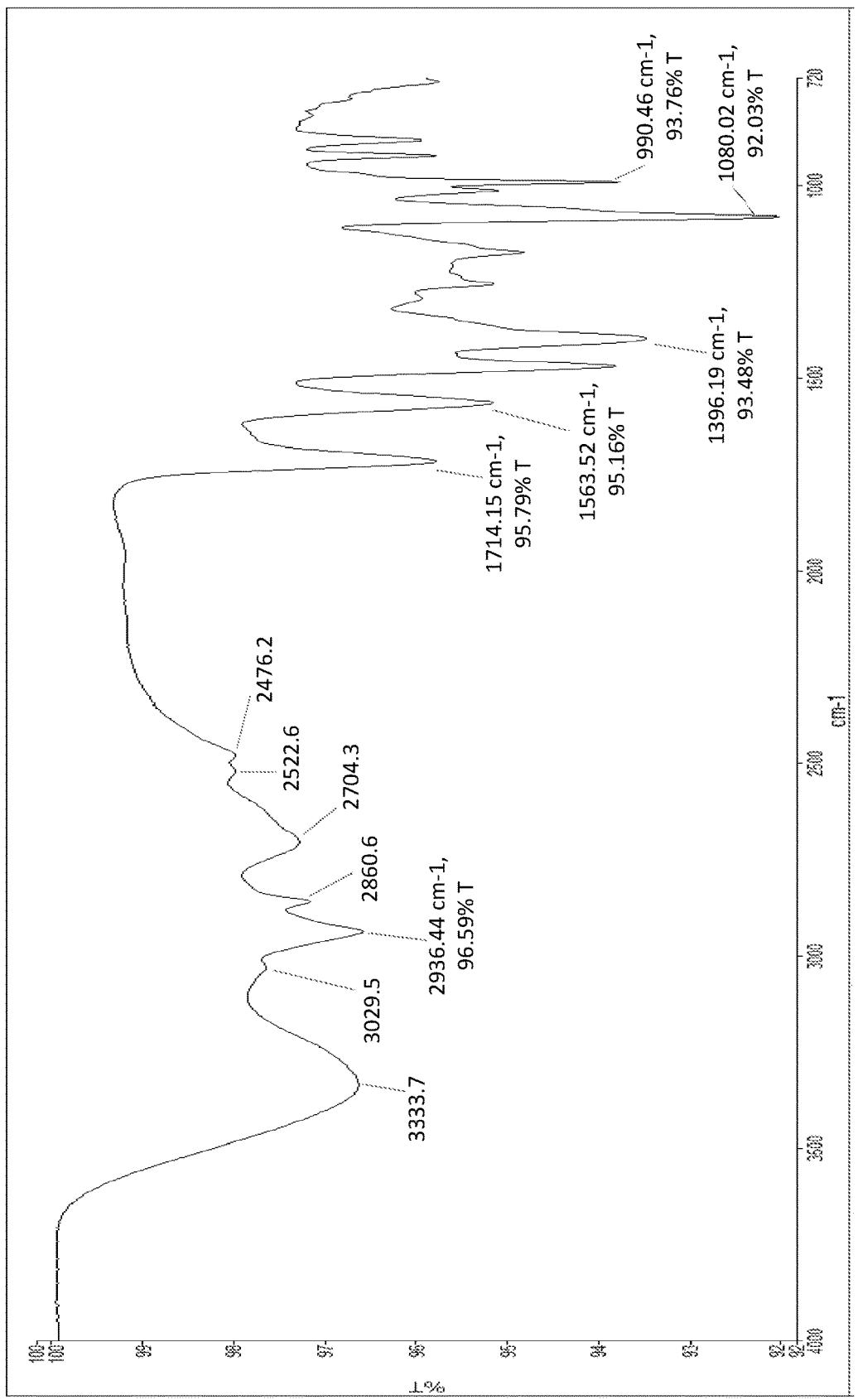
FIG. 11 illustrates the FT-IR spectrum of suberic acid & DMAE.
Figure 12:
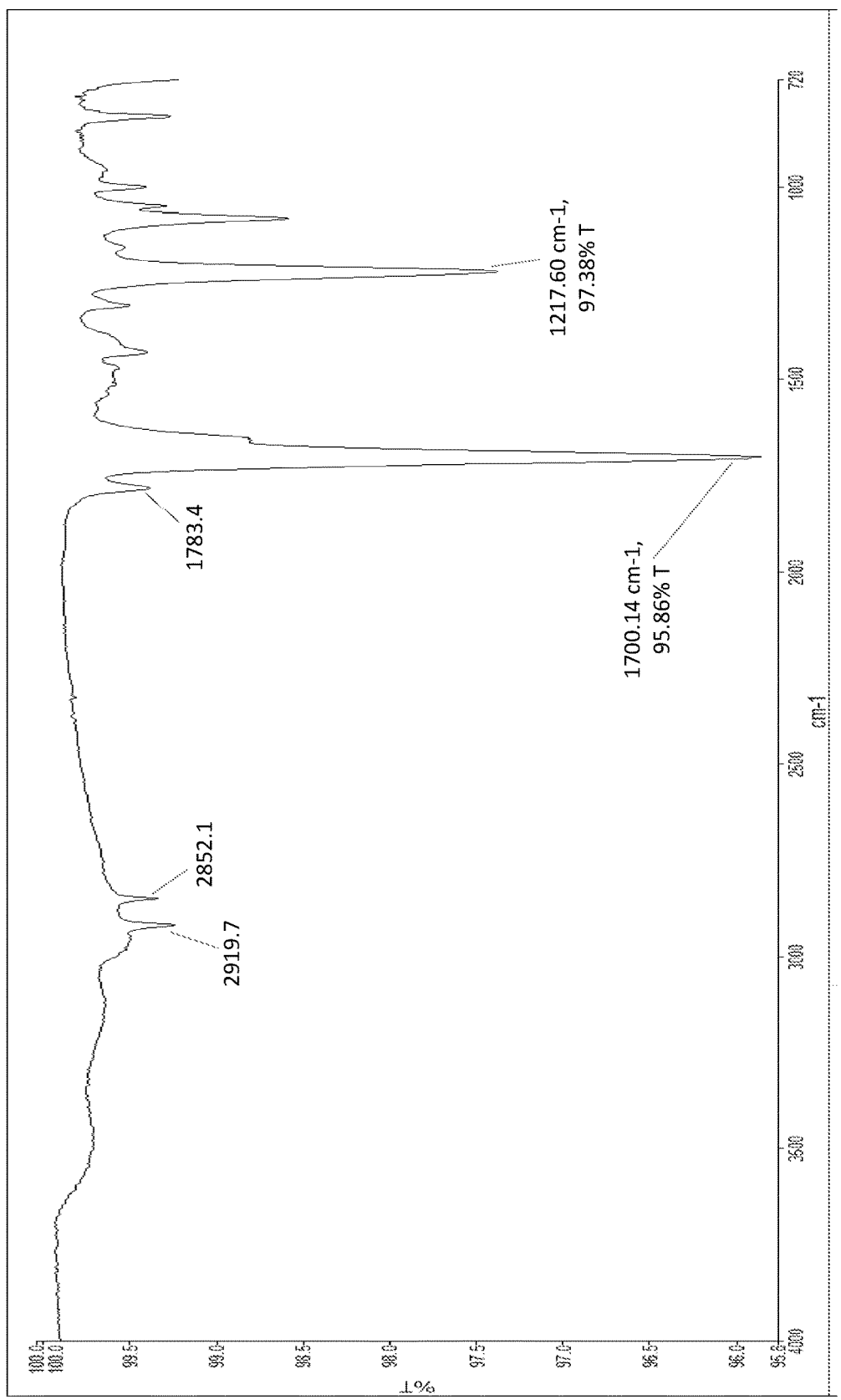
FIG. 12 illustrates the FT-IR spectrum of NHS.
Figure 13:
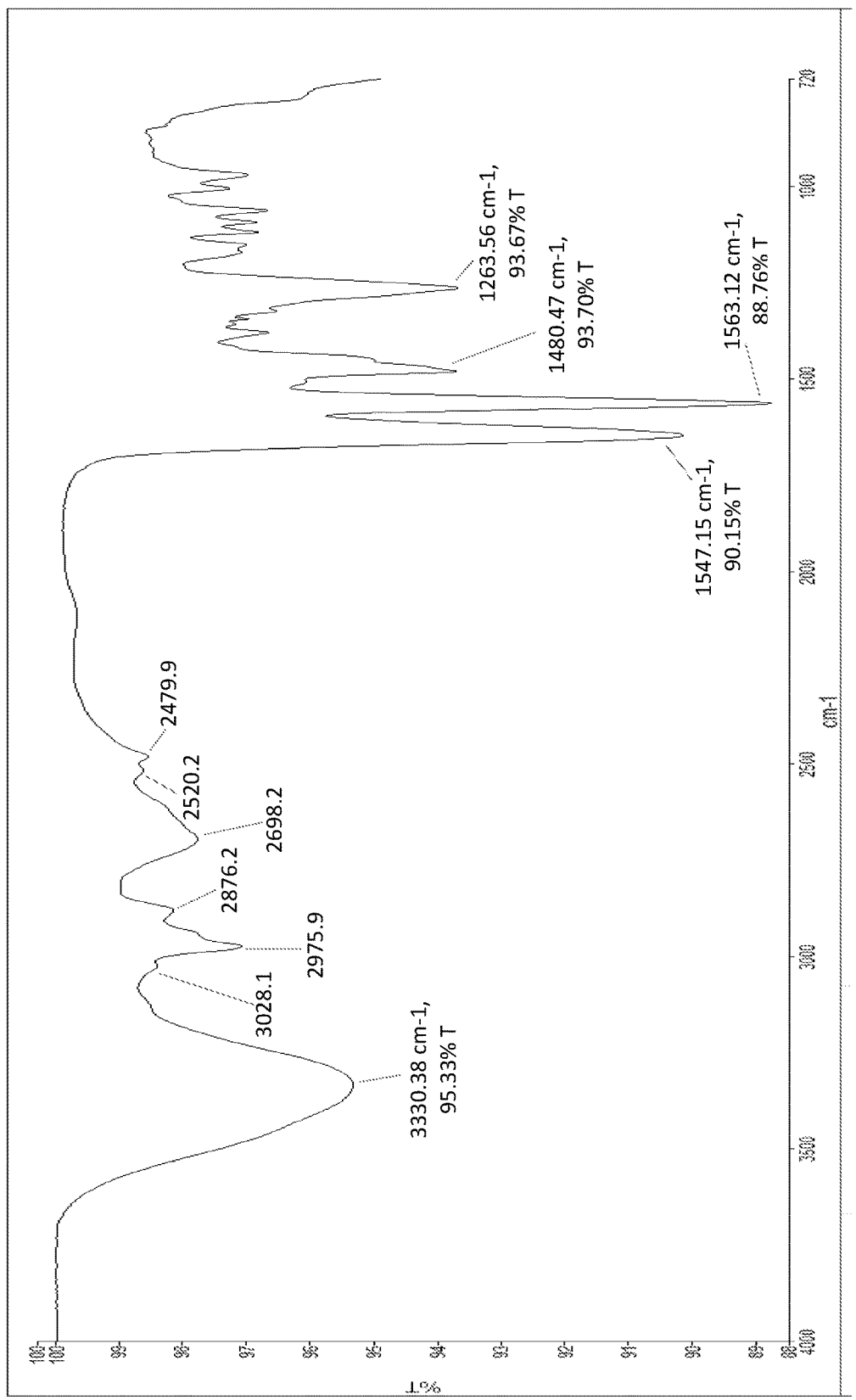
FIG. 13 illustrates the FT-IR spectrum of EDCI.
Figure 14:
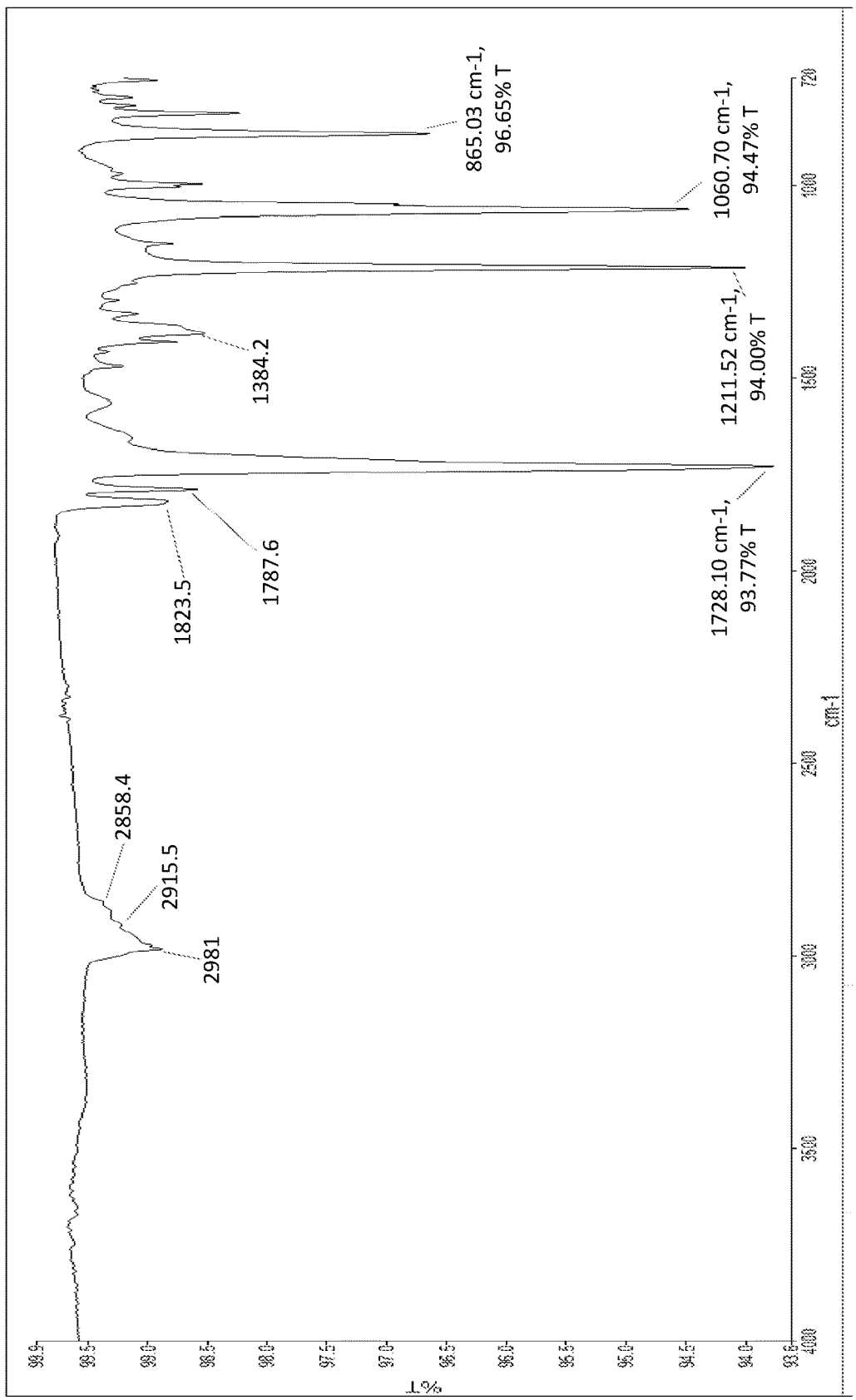
FIG. 14 illustrates the FT-IR spectrum of the precipitate formed in the forms in the 1:1:1 EDCI/NHS/suberic acid treatment solution.

As well as being an active reaction, it is also susceptible to undergo side reactions: hydrolysis (FIG. 9) and decomposition reactions (FIG. 10).

The mechanisms support the idea of using the treatment solutions immediately after mixing.

The FT-IR spectra suggest a similarity between the NHS and the precipitate. But also that the precipitate spectra exhibit characteristic NHS-ester peaks at 1823.5 cm$^{-1}$ and 1787.6 cm$^{-1}$ which suggest that the precipitate is an NHS-ester (FIGS. 11 to 14).

Figure 15:
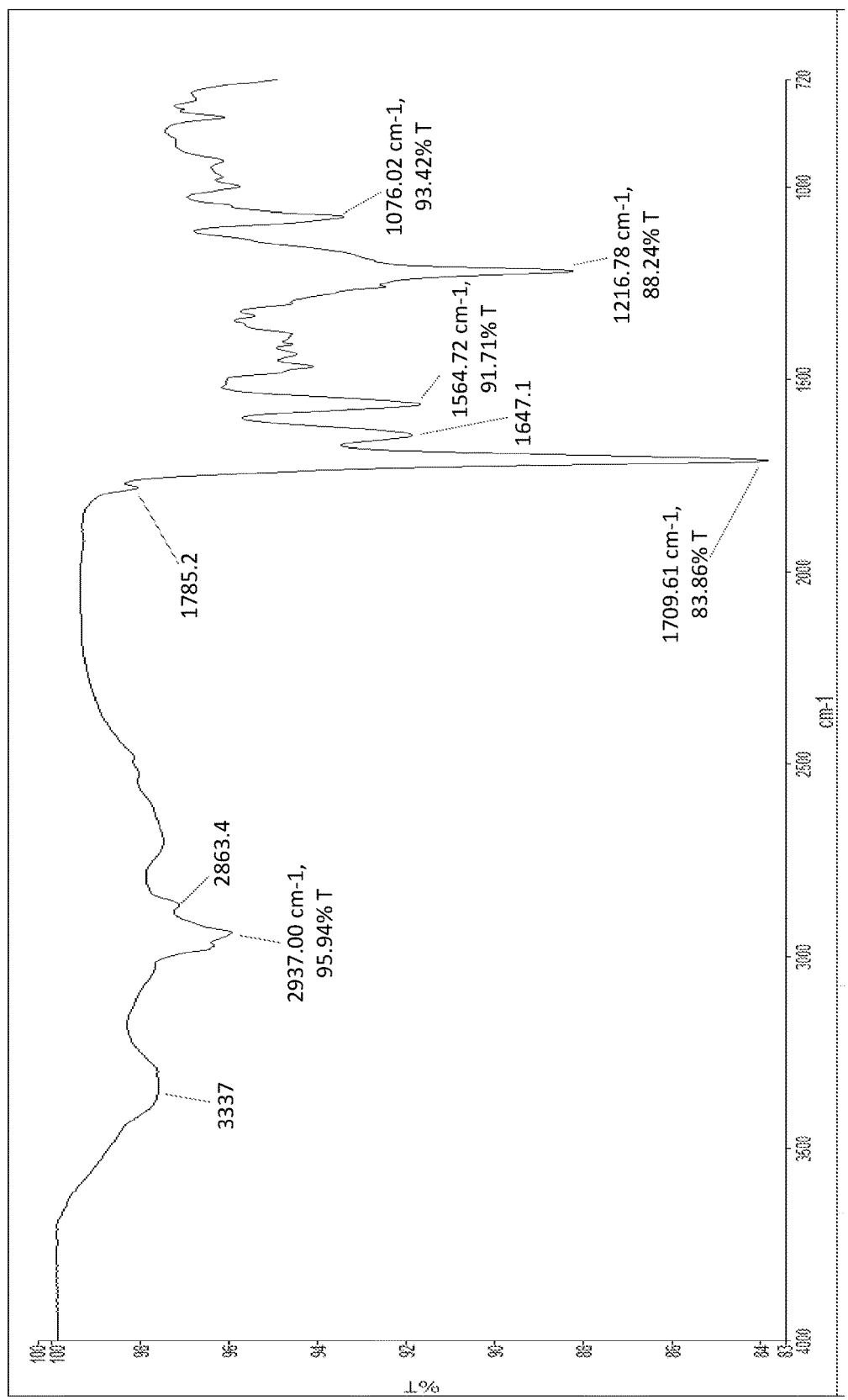
FIG. 15 illustrates the FT-IR spectrum of the treatment solution immediately after mixing.
Figure 16:
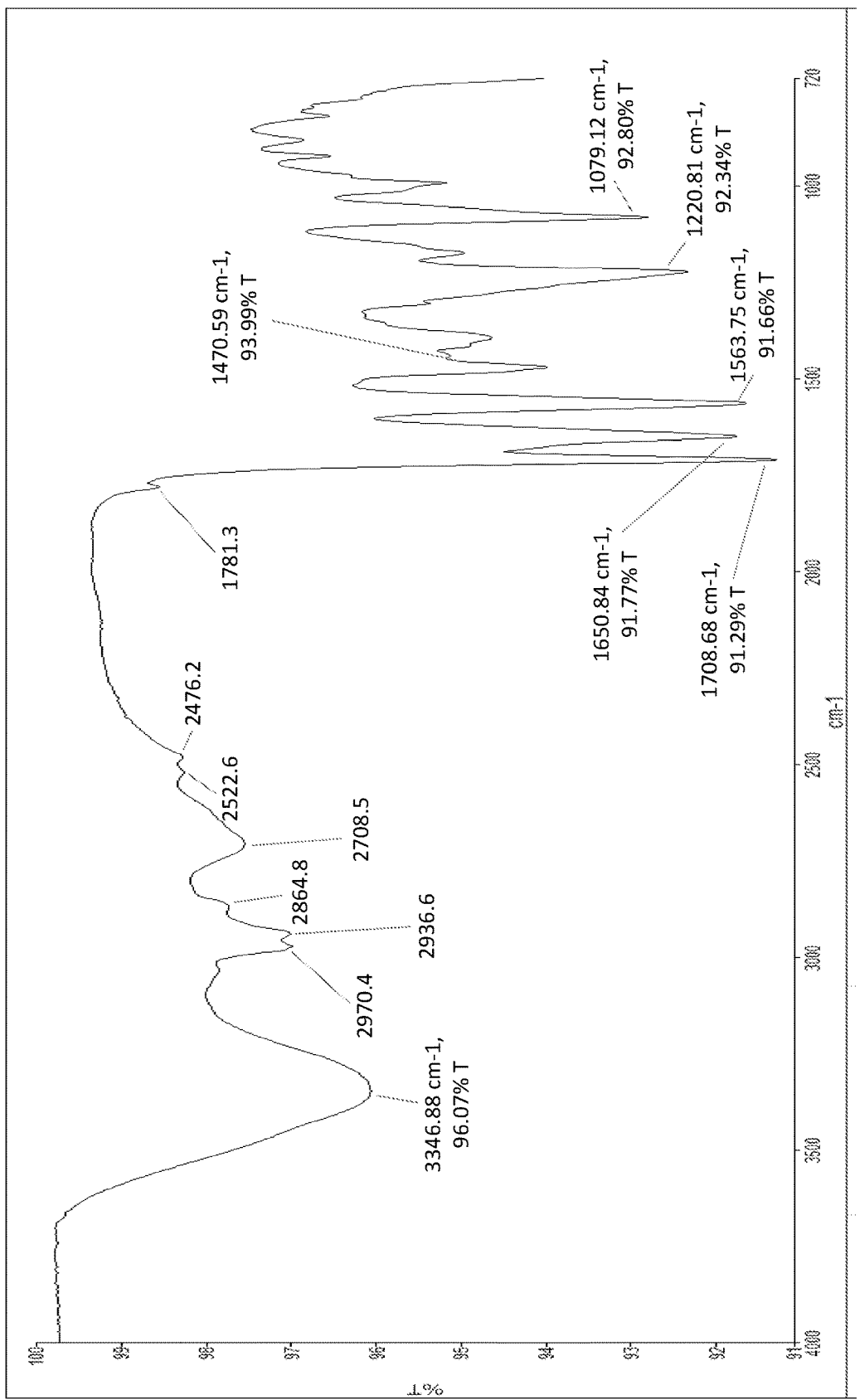
FIG. 16 illustrate the FT-IR spectrum of the treatment solution after precipitate removal.

It was also noted that the filtrate contained all the composite peaks found in the individual moieties, including the NHS (FIGS. 15 and 16).

From yield experiments, the precipitate has given an approximately 20% yield. This means that the majority of the NHS is still in solution and is still active.

While specific embodiments of the invention have been described herein for the purpose of reference and illustration, various modifications will be apparent to a person skilled in the art without departing from the scope of the invention as defined by the appended claims.

Figure 17:
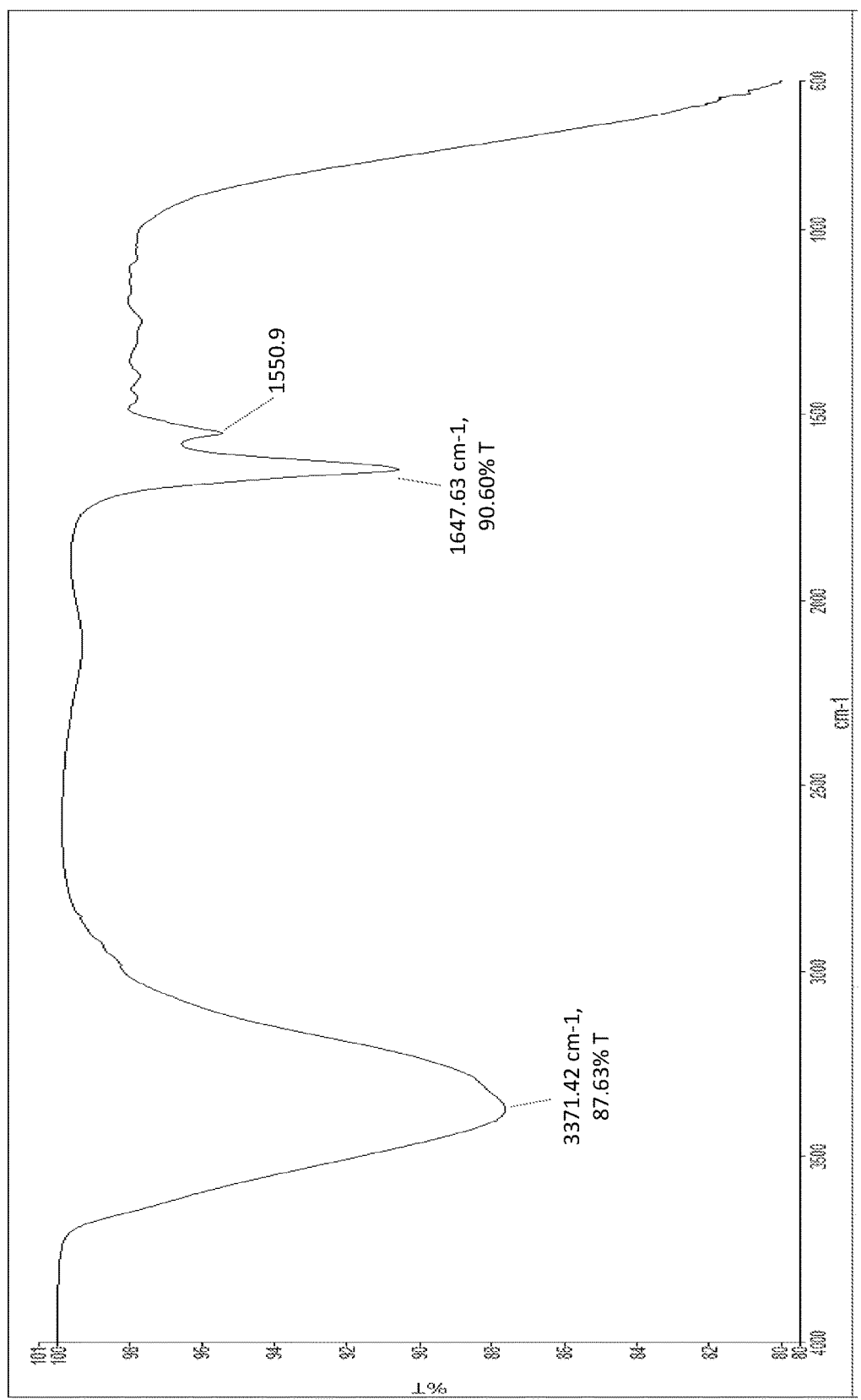
FIG. 17 illustrates the FT-IR spectrum of untreated cornea.
Figure 18:
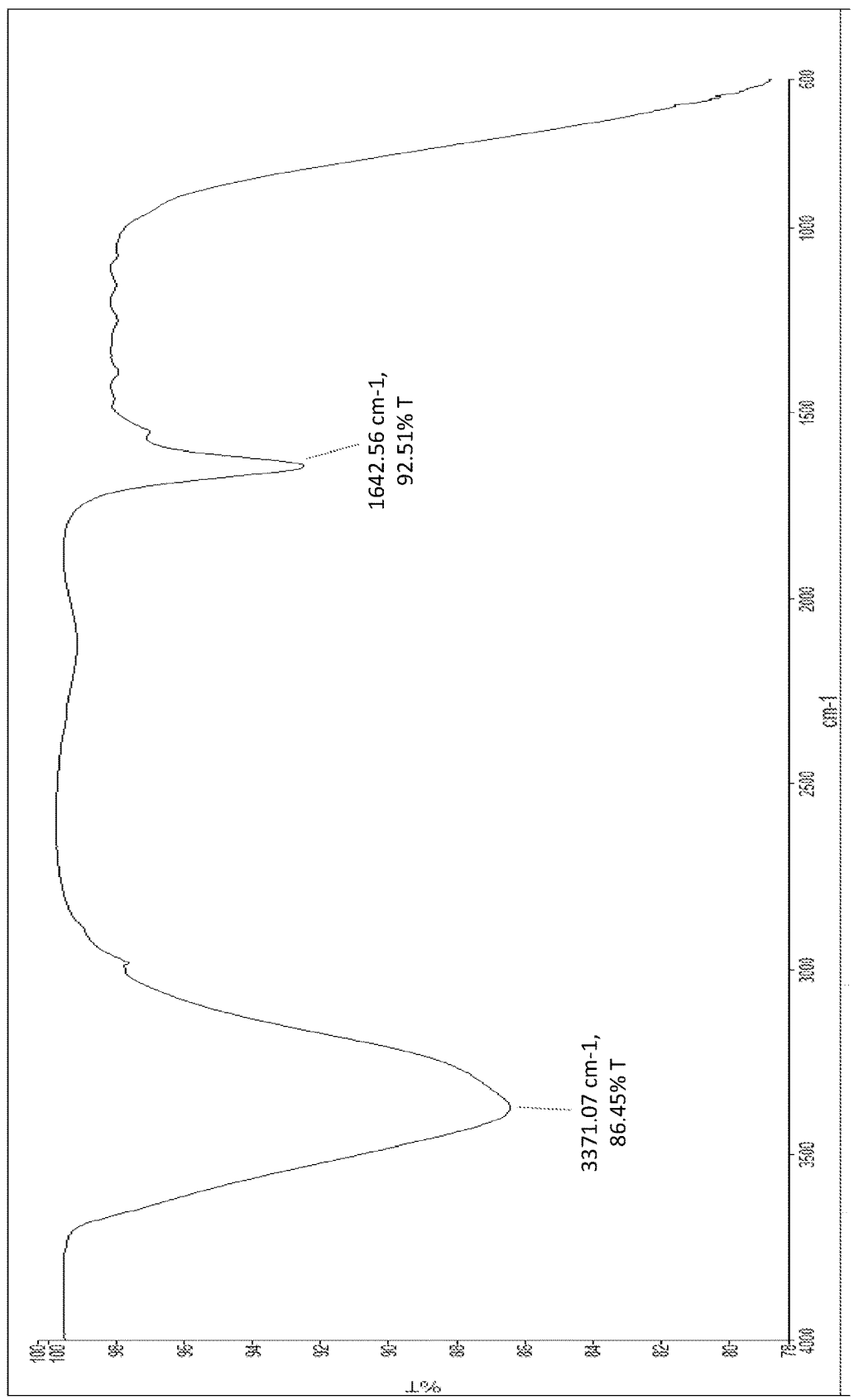
FIG. 18 illustrates the FT-IR spectrum of 1:1:1 EDCI/NHS/Suberic acid filtrate treated cornea.
Figure 19:
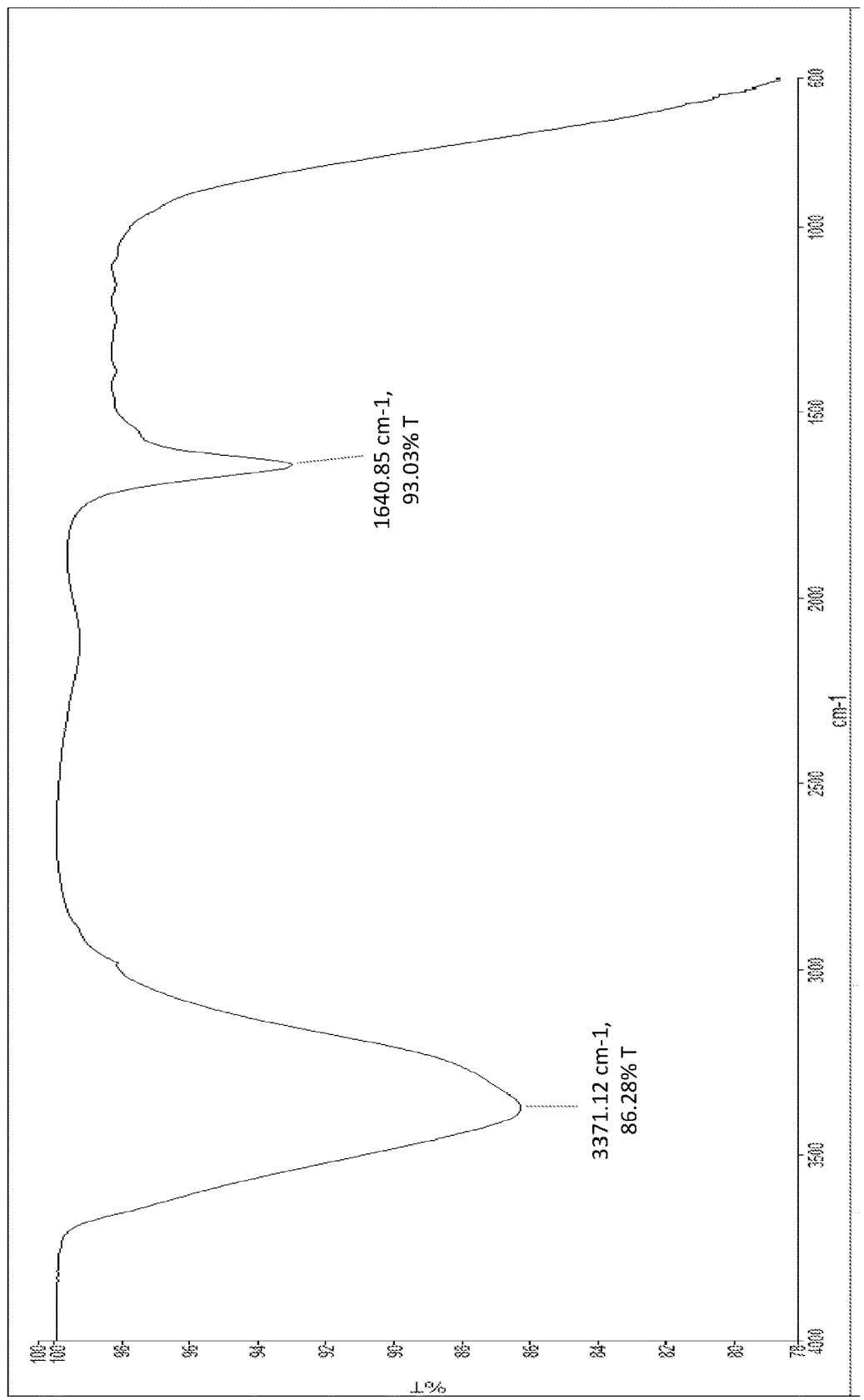
FIG. 19 illustrates the FT-IR spectrum of solubilised NHS-ester treated cornea.
Figure 20:
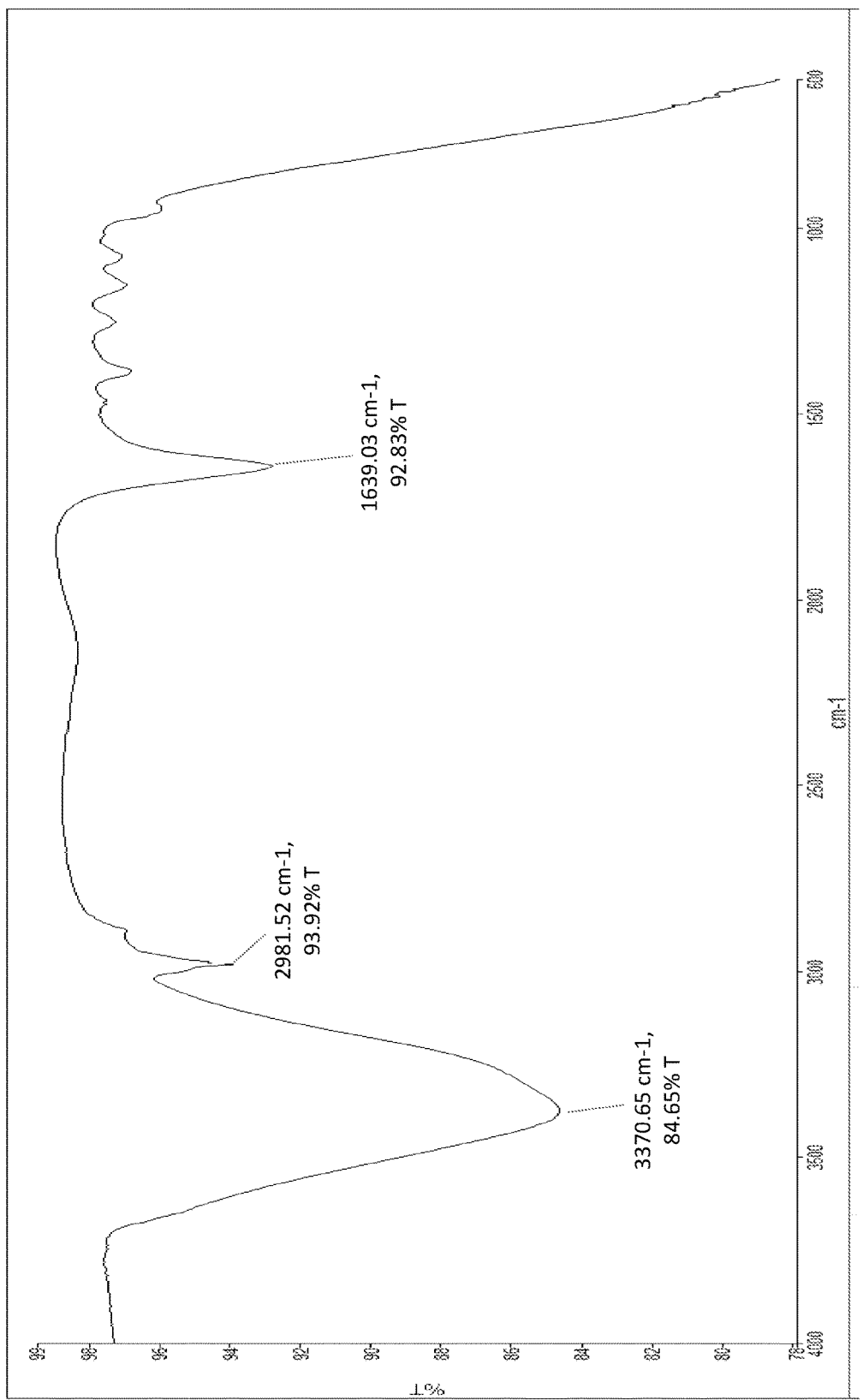
FIG. 20 illustrates the FT-IR spectrum of 1:1:1 EDCI/NHS/Suberic acid treated cornea.
Figure 21:
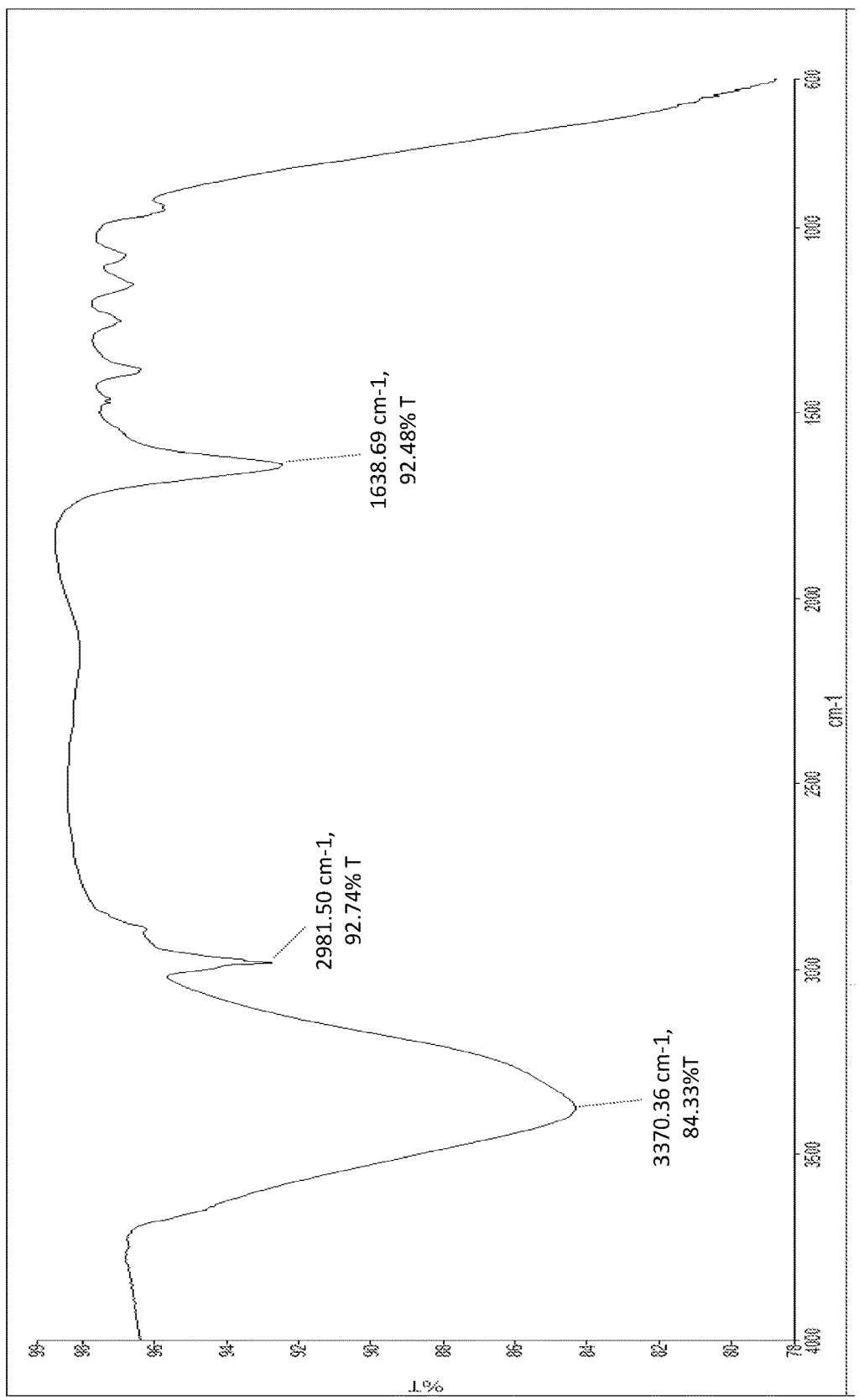
FIG. 21 illustrates the FT-IR spectrum of $BS(PEG)_5$ treated cornea.

Treatment of porcine cornea with the filtrate and the solubilised NHS-ester suggest some chemical change has occurred in the cornea in comparison to the untreated cornea (FIG. 17). The characteristic amide N—H peak found in the untreated cornea at 1550 cm$^{-1}$ is weakly present in the filtrate treated cornea (FIG. 18), and not present at all in the NHS-ester treated cornea (FIG. 19), similar to the 1:1:1 EDCI/NHS/Suberic acid treated cornea (FIG. 20) and BS(PEG)$_5$ treated cornea (FIG. 21).

Figure 22:
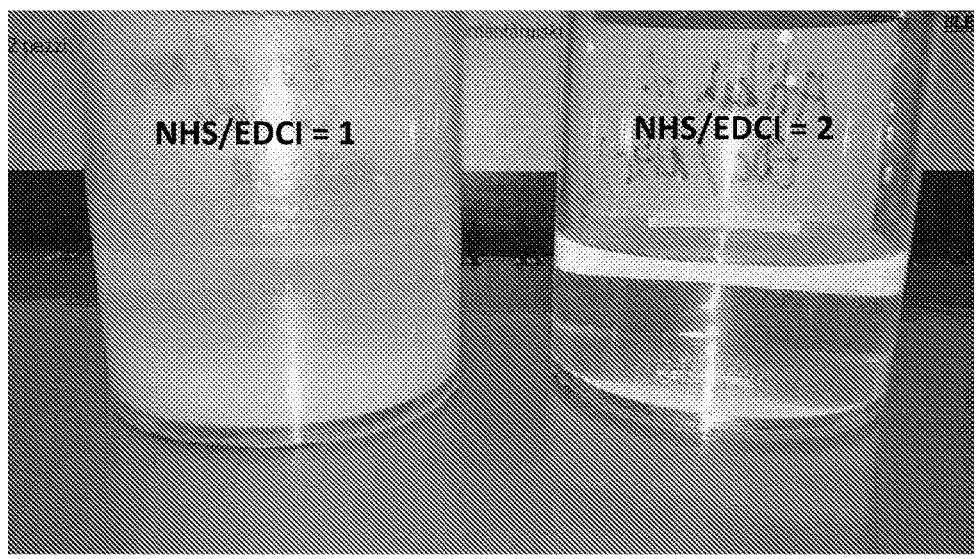
FIG. 22 illustrates photos of the treatment solutions with different NHS/EDCI molar ratios after allowing the precipitate to settle overnight.
Figure 22:
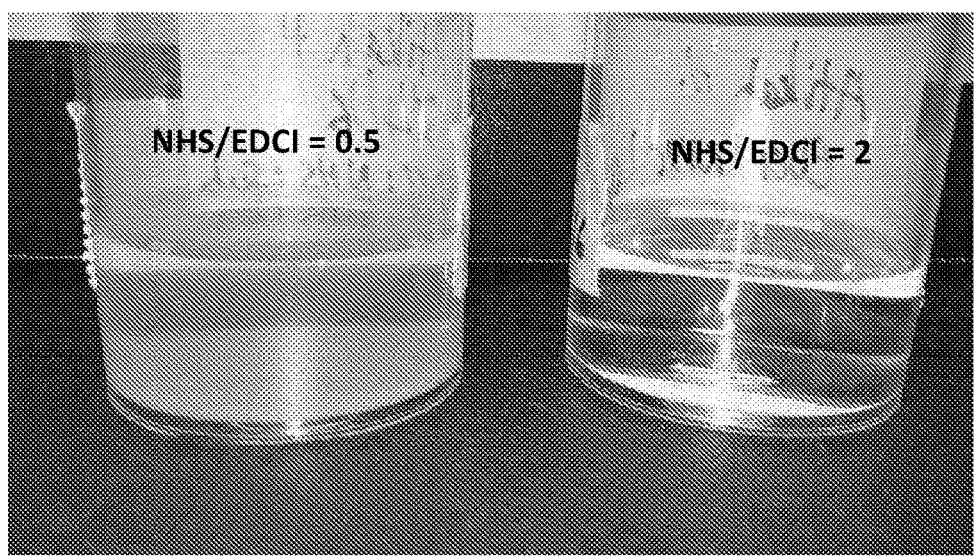
Figure 23:
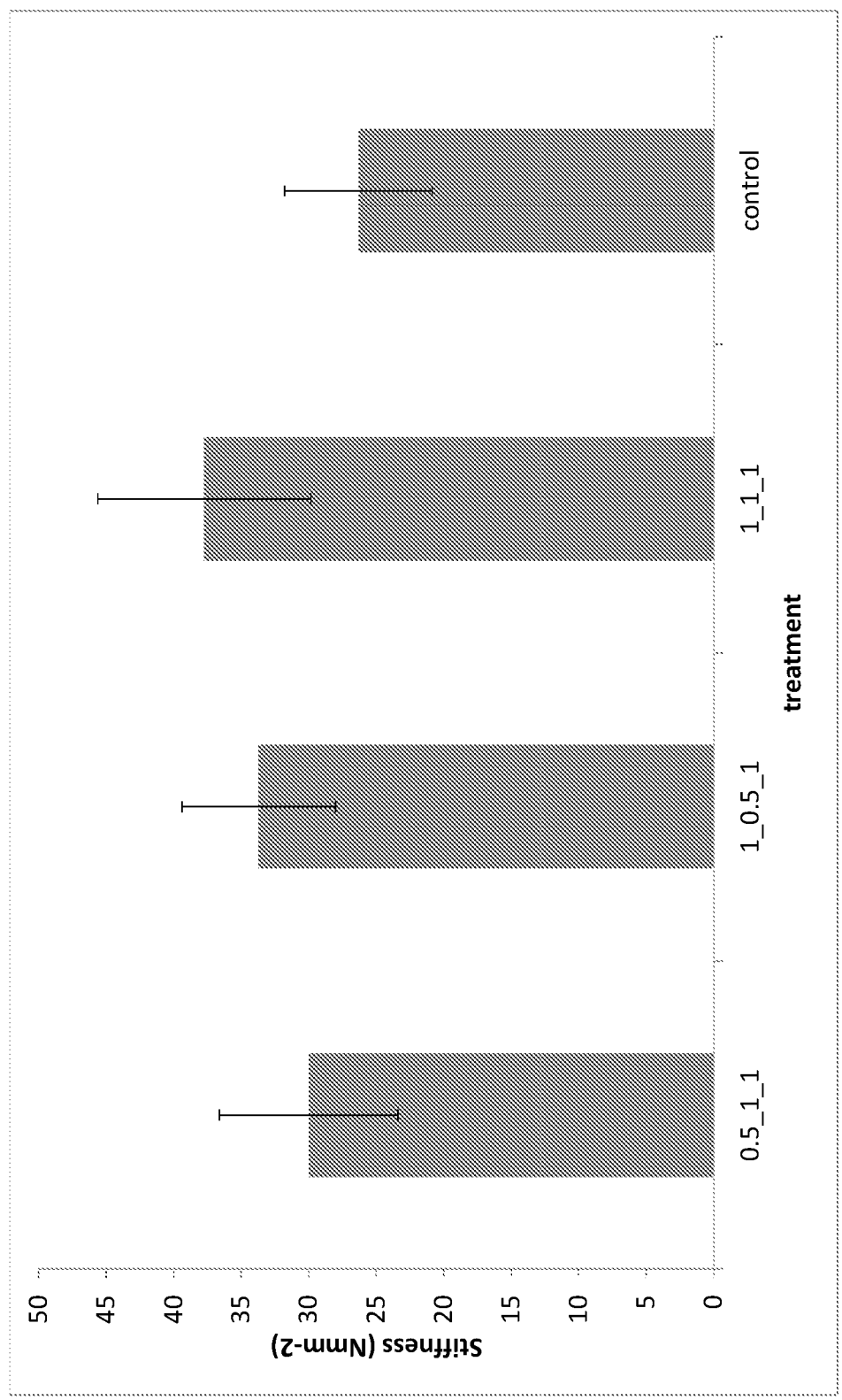
FIG. 23 illustrates the mean stiffness (±sd, n=4) for pig corneas treated with: fresh 0.5:1:1 EDCI/NHS/suberic acid treatment; 1:0.5:1 EDCI/NHS/suberic acid treatment; 1:1:1, EDCI/NHS/suberic acid treatment and a control (untreated corneas).

The NHS/EDCI=2 solution did not form a precipitate (FIG. 22). The NHS/EDCI=0.5 solutions did result in the formation of a precipitate with 18% yield, which is similar to the 1:1:1 solution which formed a precipitate with a 22% yield.

Figure 24:
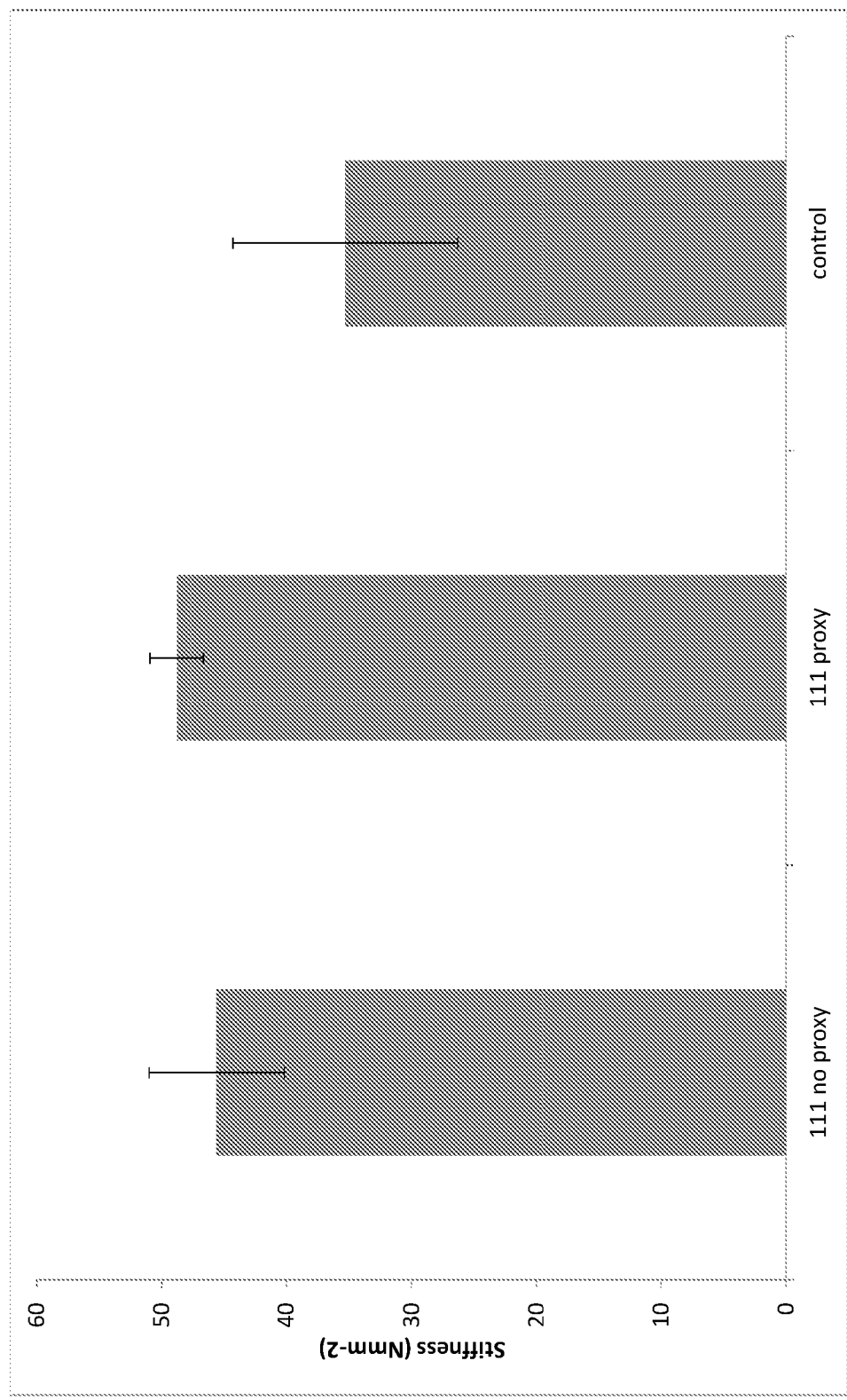
FIG. 24 illustrates the mean stiffness (±sd, n=5) for pig corneas with and without proxymetacaine pretreatment followed by crosslinking with 111 EDCI/NHS/suberic acid solution and a control (untreated corneas).

Pre-treatment of corneas with proxymetacaine "111proxy" before crosslinking with the 1:1:1 solution resulted in a slight increase in stiffness in comparison to the standard 1:1:1 treatment but this was not significant (FIG. 24).

Figure 25:
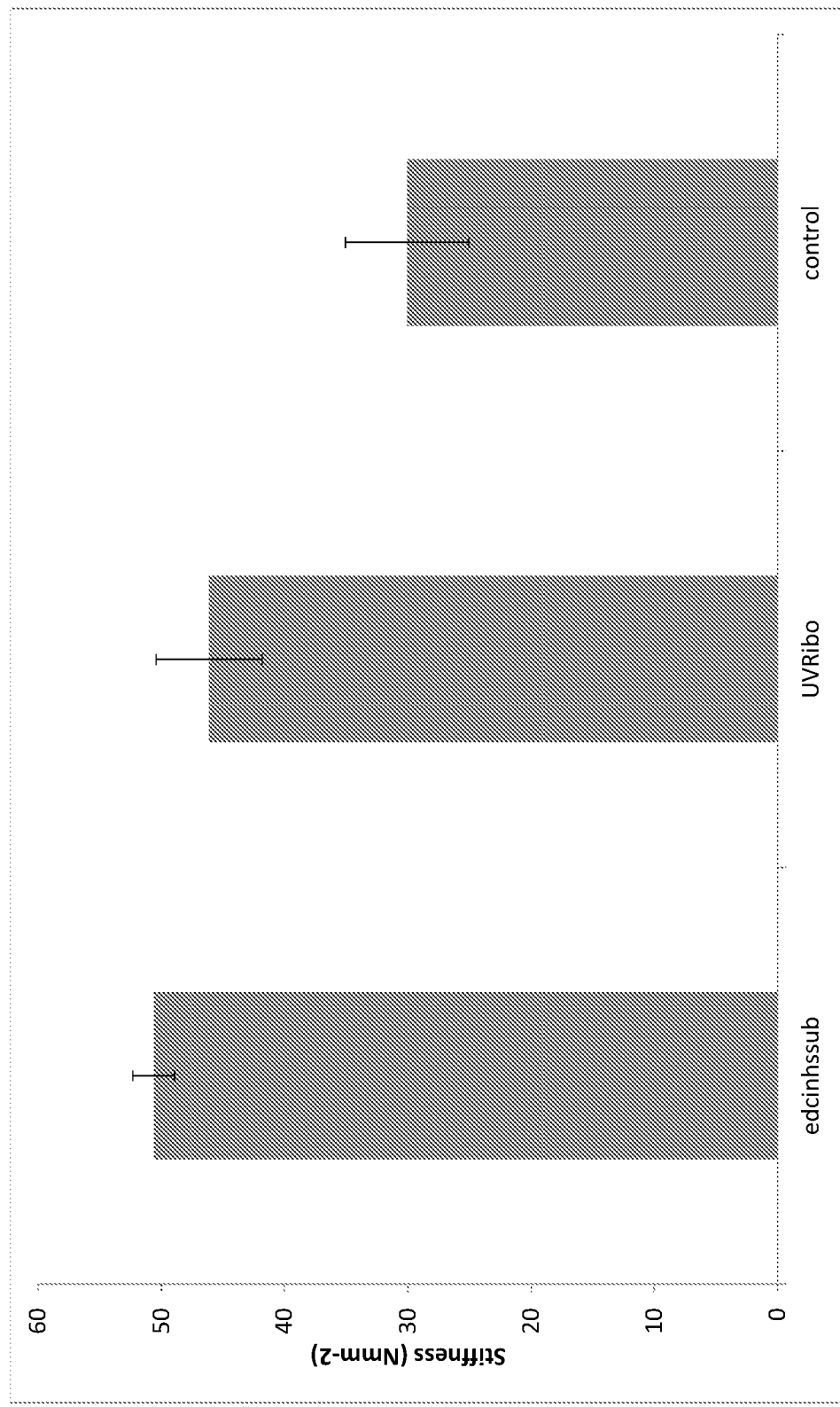
FIG. 25 illustrates the mean stiffness (±sd, n=4) for pig stromas treated with: 1:1:1 EDCI/NHS/Suberic acid; UV/riboflavin; and a control (untreated corneas).

Tensile tests showed the 1:1:1 treatment of the stroma exhibited highest stiffness, with 67% difference, while UV/riboflavin exhibited 53% difference (FIG. 25) in comparison to the control untreated stroma. There is approximately 10% difference between the treatments.

While specific embodiments of the invention have been described herein for the purpose of reference and illustration, various modifications will be apparent to a person skilled in the art without departing from the scope of the invention as defined by the appended claims.

The invention claimed is:
1. A pharmaceutical composition suitable for administration to the eye comprising:

(i) an aqueous vehicle; and (ii) a non-toxic, water soluble cross-linker, or a pharmaceutically acceptable salt thereof, dissolved in the aqueous vehicle;

wherein the composition has a pH within the range of 6 to 9;

wherein the non-toxic, water soluble cross-linker is a compound of Formula (I) shown below:

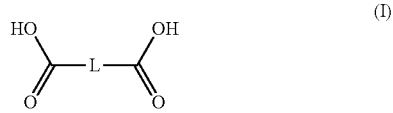

wherein L is:

(a) a linear or branched (1-12C)alkylene linker that optionally comprises one or more heteroatoms selected from N, O or S, and is optionally substituted with one or more groups selected from carboxy, anhydride, oxo, halo, trifluoromethyl, cyano, nitro, hydroxy, mercapto, amino, (1-6C)alkyl, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, (2-6C)alkanoyl, or (2-6C)alkanoyloxy, or (b) a water soluble polymeric chain; and wherein the pharmaceutical composition is administered in combination with one or more peptide coupling agents either prior to, during or following the administration of the pharmaceutical composition to the eye.

2. A pharmaceutical composition according to claim 1, wherein the non-toxic, water soluble cross-linker comprises 2 to 4 carboxyl groups.

3. A pharmaceutical composition according to claim 1, wherein the non-toxic, water soluble cross-linker is a compound of formula (I), or a pharmaceutically acceptable salt and/or solvate thereof, and wherein L is a (2-8C)alkyl optionally substituted with one or more groups of the formula —(CH$_2$)$_n$CO$_2$H, wherein n is an integer of between 0 and 10; or L is a polyethylene glycol chain.

4. A pharmaceutical composition according to claim 1, wherein the non-toxic, water soluble cross-linker is selected from sebacic, azelaic, suberic, pimelic, adipic, glutaric or succinic acid.

5. A pharmaceutical composition according to claim 1, wherein the composition further comprises a buffer to maintain the pH of the composition within the range of pH 6 to 9.

6. A pharmaceutical composition according to claim 1, wherein the composition further comprises one or more carbodiimide peptide coupling reagents.

7. A method of treating a collagenic eye disorder associated with the weakening, degradation and/or damage to collagen in the cornea and/or sclera of the eye, said method comprising administering to a human or animal subject in need of such treatment a therapeutically effective amount of a pharmaceutical composition comprising a non-toxic, water soluble cross-linker comprising two or more carboxyl groups or a pharmaceutically acceptable salt thereof, wherein the non-toxic, water soluble cross-linker is a compound of Formula (I) shown below:

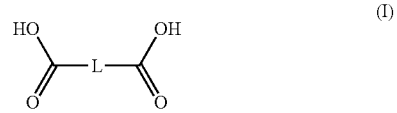

wherein L is:

(a) a linear or branched (1-12C)alkylene linker that optionally comprises one or more heteroatoms selected from N, O or S, and is optionally substituted with one or more groups selected from carboxy, anhydride, oxo, halo, trifluoromethyl, cyano, nitro, hydroxy, mercapto, amino, (1-6C)alkyl, (1-6C)alkoxy, (1-6C)alkylthio, (1-6C)alkylsulphinyl, (1-6C)alkyl sulphonyl, (1-6C) alkylamino, di-[(1-6C)alkyl]amino, (1-6C)alkoxycarbonyl, (2-6C)alkanoyl, or (2-6C)alkanoyloxy, or (b) a water soluble polymeric chain;

wherein the cross-linker is administered in combination with one or more peptide coupling reagents.

8. A method according to claim 7, wherein the collagenic eye disorder is selected from:

(a). corneal ectasia;

(b). inflammation in the eye caused by infective, traumatic (chemical, physical, thermal, surgical) or immune-mediated corneal or scleral disease;

(c). re-shaping the eye, optionally following transplant or surgery;

(d). corneal swelling due to corneal oedema;

(e). mechanically strengthening a weakened sclera in the treatment of myopia and/or glaucoma.

9. A method according to claim 7, wherein the collagenic eye disorder is keratoconus.

10. A device for administering the pharmaceutical composition of claim 1, the device comprising:

(i). a first compartment comprising the pharmaceutical composition of claim 1;

(ii). a second compartment comprising one or more peptide coupling agents, and optionally an activator, dissolved in a suitable pharmaceutically acceptable vehicle;

wherein the device is configured to mix at least a proportion of the contents of the first and second compartments either prior to or during dispensing to the eye.

11. The pharmaceutical composition according to claim 1, wherein the one or more peptide coupling agents are present in a separate aqueous formulation that is mixed with the pharmaceutical composition, either prior to, during or following the administration of the pharmaceutical composition to the eye.

12. A pharmaceutical composition according to claim 1, wherein the pharmaceutical composition is administered in combination with the one or more peptide coupling agents and one or more activating agents.

13. The pharmaceutical composition according to claim 11, wherein one or more activating agents are present in the separate aqueous formulation comprising the one or more peptide coupling agents.

14. The pharmaceutical composition of claim 13, concentration of the activating agent is between 0 and 1.0 molL$^{-1}$.

15. The pharmaceutical composition of claim 1, wherein the concentration of the cross-linker is between 0.1 and 25 mM.

16. The pharmaceutical composition of claim 1, the concentration of the peptide coupling agent is between 0 and 1.0 molL$^{-1}$.

17. The method of claim 8, wherein the collagenic eye disorder is non-inflammatory corneal ectasia selected from (i) non-inflammatory corneal extasia; (ii) inflammatory corneal ectasia; (iii) iatrogenic corneal ectasia (keratectasia); or (iv) myopia.

18. The method of claim 17, wherein the collagenic eye disorder is keratoglobus, or pellucid marginal degeneration.

19. The method of claim 8, wherein the collagenic eye disorder is inflammation in the eye caused by immune-mediated vasculitic corneal or scleral disease.

20. The method of claim 8, wherein the collagenic eye disorder is corneal swelling due to bullous keratopathy, fuchs endothelial dystrophy, congenital hereditary endothelial dystrophy, or hydrops of the cornea in keratoconus.

\* \* \* \* \*